(12) United States Patent
Sweeney

(10) Patent No.: US 8,396,553 B2
(45) Date of Patent: *Mar. 12, 2013

(54) SYSTEM AND METHOD FOR CONDITIONAL BIVENTRICULAR PACING

(75) Inventor: Michael O. Sweeney, Newton, MA (US)

(73) Assignee: Medtronic, Inc., Minneapolis, MN (US)

( * ) Notice: Subject to any disclaimer, the term of this patent is extended or adjusted under 35 U.S.C. 154(b) by 418 days.

This patent is subject to a terminal disclaimer.

(21) Appl. No.: 12/713,517

(22) Filed: Feb. 26, 2010

(65) Prior Publication Data

US 2010/0222839 A1 Sep. 2, 2010

Related U.S. Application Data

(60) Provisional application No. 61/156,177, filed on Feb. 27, 2009.

(51) Int. Cl.
*A61N 1/365* (2006.01)
*A61N 1/00* (2006.01)

(52) U.S. Cl. ................. 607/17; 607/9; 607/14

(58) Field of Classification Search ............ 607/17
See application file for complete search history.

(56) References Cited

U.S. PATENT DOCUMENTS

| 3,057,356 A | 10/1962 | Greatbatch |
|---|---|---|
| 3,253,596 A | 5/1966 | Keller |
| 3,478,746 A | 11/1969 | Greatbatch |
| 3,595,242 A | 7/1971 | Berkovits |
| 3,648,707 A | 3/1972 | Greatbatch |
| 3,747,604 A | 7/1973 | Berkovits |
| 4,312,355 A | 1/1982 | Funke |
| 4,386,610 A | 6/1983 | Leckrone |
| 4,428,378 A | 1/1984 | Anderson et al. |
| 4,432,362 A | 2/1984 | Leckrone et al. |
| 4,476,868 A | 10/1984 | Thompson |
| 4,523,593 A | 6/1985 | Rueter et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallok |
| 4,856,523 A | 8/1989 | Sholder et al. |
| 4,856,524 A | 8/1989 | Baker |
| 4,880,005 A | 11/1989 | Pless et al. |
| 4,890,617 A | 1/1990 | Markowitz et al. |

(Continued)

FOREIGN PATENT DOCUMENTS

| EP | 0363015 | 4/1990 |
|---|---|---|
| EP | 0448193 | 9/1991 |

(Continued)

OTHER PUBLICATIONS

Sweeney, Michael O., "Therapeutic Minimization of Ventricular Pacing to Prevent Atrial Fibrillation, Heart Failure, and Death". Cardiology Rounds, Snell Publications, Mar. 2005, vol. 9, Issue 3.*

(Continued)

*Primary Examiner* — Carl H Layno
*Assistant Examiner* — Erin Piateski
(74) *Attorney, Agent, or Firm* — Michael C. Soldner

(57) ABSTRACT

A medical device having a plurality of electrodes sensing cardiac signals, and a microprocessor operably coupled to the plurality of electrodes and configured to determine a cumulative atrioventricular interval (AVI) burden in response to the sensed cardiac signals, and to switch operation of the device between a minimal biventricular pacing (MBVP) mode and a conditional triple chamber pacing (CTCP) mode in response to the determined AVI burden.

26 Claims, 10 Drawing Sheets

U.S. PATENT DOCUMENTS

| | | | |
|---|---|---|---|
| 4,932,046 A | 6/1990 | Katz et al. | |
| 4,941,471 A | 7/1990 | Mehra | |
| 4,953,551 A | 9/1990 | Mehra et al. | |
| 4,967,746 A | 11/1990 | Vandegriff | |
| 5,052,388 A | 10/1991 | Sivula et al. | |
| 5,085,215 A | 2/1992 | Nappholz et al. | |
| 5,097,832 A | 3/1992 | Buchanan | |
| 5,117,824 A | 6/1992 | Keimel et al. | |
| 5,133,350 A | 7/1992 | Duffin | |
| 5,144,950 A | 9/1992 | Stoop et al. | |
| 5,163,427 A | 11/1992 | Keimel | |
| 5,188,105 A | 2/1993 | Keimel | |
| 5,188,117 A | 2/1993 | Steinhaus et al. | |
| 5,228,438 A | 7/1993 | Buchanan | |
| 5,273,035 A | 12/1993 | Markowitz et al. | |
| 5,292,340 A | 3/1994 | Crosby et al. | |
| 5,318,594 A | 6/1994 | Limousin et al. | |
| 5,334,220 A | 8/1994 | Sholder | |
| 5,345,362 A | 9/1994 | Winkler | |
| 5,350,409 A * | 9/1994 | Stoop et al. | 607/17 |
| 5,372,607 A | 12/1994 | Stone et al. | |
| 5,388,586 A | 2/1995 | Lee et al. | |
| 5,417,714 A | 5/1995 | Levine et al. | |
| 5,522,859 A | 6/1996 | Stroebel et al. | |
| 5,540,725 A | 7/1996 | Bornzin et al. | |
| 5,584,868 A | 12/1996 | Salo et al. | |
| 5,591,214 A | 1/1997 | Lu | |
| 5,626,623 A | 5/1997 | Kieval et al. | |
| 5,632,716 A | 5/1997 | Biu et al. | |
| 5,643,326 A | 7/1997 | Weiner et al. | |
| 5,658,237 A | 8/1997 | Francischelli | |
| 5,674,257 A | 10/1997 | Stroebel et al. | |
| 5,697,958 A | 12/1997 | Paul et al. | |
| 5,725,561 A | 3/1998 | Stroebel et al. | |
| 5,741,308 A | 4/1998 | Sholder et al. | |
| 5,814,077 A | 9/1998 | Sholder et al. | |
| 5,836,974 A | 11/1998 | Christini et al. | |
| 5,861,007 A | 1/1999 | Hess et al. | |
| 5,873,895 A | 2/1999 | Sholder et al. | |
| 5,954,755 A | 9/1999 | Casavant | |
| 5,999,850 A | 12/1999 | Dawson et al. | |
| 6,058,326 A | 5/2000 | Hess et al. | |
| 6,058,328 A | 5/2000 | Levine et al. | |
| 6,122,546 A * | 9/2000 | Sholder et al. | 607/9 |
| 6,128,529 A | 10/2000 | Esler et al. | |
| 6,128,534 A | 10/2000 | Park et al. | |
| 6,141,586 A | 10/2000 | Mower | |
| 6,169,918 B1 | 1/2001 | Haefner et al. | |
| 6,198,968 B1 | 3/2001 | Prutchi et al. | |
| 6,256,541 B1 | 7/2001 | Heil et al. | |
| 6,321,115 B1 | 11/2001 | Mouchawar et al. | |
| 6,397,105 B1 | 5/2002 | Bouhour et al. | |
| 6,434,424 B1 | 8/2002 | Igel et al. | |
| 6,442,429 B1 * | 8/2002 | Hill et al. | 607/14 |
| 6,477,416 B1 | 11/2002 | Florio et al. | |
| 6,493,583 B1 * | 12/2002 | Levine et al. | 607/9 |
| 6,556,859 B1 | 4/2003 | Wohlgemuth et al. | |
| 6,609,028 B2 | 8/2003 | Struble | |
| 6,650,937 B2 | 11/2003 | Kerver | |
| 6,654,637 B2 * | 11/2003 | Rouw et al. | 607/7 |
| 6,697,673 B1 | 2/2004 | Lu | |
| 6,731,980 B1 | 5/2004 | Mouchawar et al. | |
| 6,748,269 B2 * | 6/2004 | Thompson et al. | 607/4 |
| 6,772,005 B2 | 8/2004 | Casavant et al. | |
| 6,792,307 B1 | 9/2004 | Levine et al. | |
| 6,873,875 B1 | 3/2005 | Gilkerson et al. | |
| 6,904,315 B2 | 6/2005 | Panken et al. | |
| 6,925,326 B1 | 8/2005 | Levine et al. | |
| 6,970,743 B2 | 11/2005 | Weinberg et al. | |
| 6,978,175 B1 | 12/2005 | Florio et al. | |
| 7,027,868 B2 | 4/2006 | Rueter et al. | |
| 7,082,330 B2 * | 7/2006 | Stadler et al. | 607/17 |
| 7,123,960 B2 | 10/2006 | Ding et al. | |
| 7,130,683 B2 | 10/2006 | Casavant et al. | |
| 7,130,685 B2 * | 10/2006 | Casavant et al. | 607/9 |
| 7,218,964 B2 | 5/2007 | Hill et al. | |
| 7,218,965 B2 | 5/2007 | Casavant et al. | |
| 7,245,966 B2 | 7/2007 | Betzold et al. | |
| 7,248,924 B2 | 7/2007 | Casavant | |
| 7,254,441 B2 | 8/2007 | Stroebel | |
| 7,254,442 B2 * | 8/2007 | Van Gelder et al. | 607/25 |
| 7,283,872 B2 | 10/2007 | Boute et al. | |
| 7,314,451 B2 | 1/2008 | Halperin et al. | |
| 7,381,215 B2 * | 6/2008 | Boute | 607/90 |
| 7,502,646 B2 * | 3/2009 | Sheldon et al. | 607/9 |
| 7,515,958 B2 * | 4/2009 | Sheldon et al. | 607/9 |
| 7,532,929 B2 * | 5/2009 | Mussig et al. | 607/14 |
| 7,542,799 B2 * | 6/2009 | Stoop et al. | 607/9 |
| 7,555,336 B2 * | 6/2009 | Sheth et al. | 600/509 |
| 7,640,058 B2 * | 12/2009 | Lang | 607/17 |
| 2002/0038482 A1 | 4/2002 | Mennicke et al. | |
| 2002/0041700 A1 | 4/2002 | Therbaud | |
| 2002/0082646 A1 | 6/2002 | Casavant et al. | |
| 2002/0082664 A1 | 6/2002 | Kerver | |
| 2002/0128687 A1 | 9/2002 | Baker et al. | |
| 2002/0138417 A1 | 9/2002 | Lawrence | |
| 2003/0078627 A1 | 4/2003 | Casavant et al. | |
| 2004/0010292 A1 | 1/2004 | Amblard et al. | |
| 2004/0024694 A1 | 2/2004 | Lawrence et al. | |
| 2004/0078321 A1 | 4/2004 | Lawrence | |
| 2004/0117316 A1 | 6/2004 | Gillum | |
| 2004/0158292 A1 | 8/2004 | Sheldon et al. | |
| 2004/0215273 A1 | 10/2004 | Van Bolhuis et al. | |
| 2004/0260349 A1 | 12/2004 | Stroebel | |
| 2005/0038482 A1 | 2/2005 | Yonce et al. | |
| 2005/0055059 A1 | 3/2005 | Betzold et al. | |
| 2005/0096725 A1 | 5/2005 | Seim et al. | |
| 2005/0177197 A1 * | 8/2005 | Betzold | 607/27 |
| 2005/0267539 A1 * | 12/2005 | Betzold et al. | 607/9 |
| 2005/0273430 A1 | 12/2005 | Pliha | |
| 2006/0155338 A1 * | 7/2006 | Mongeon et al. | 607/9 |
| 2006/0235478 A1 * | 10/2006 | Van Gelder et al. | 607/9 |
| 2006/0241703 A1 | 10/2006 | Ding et al. | |
| 2006/0247705 A1 | 11/2006 | Rueter et al. | |
| 2007/0005113 A1 | 1/2007 | Casavant et al. | |
| 2007/0093873 A1 * | 4/2007 | Chirife et al. | 607/17 |
| 2007/0203523 A1 * | 8/2007 | Betzold | 607/9 |
| 2007/0213777 A1 | 9/2007 | Betzold et al. | |
| 2007/0219589 A1 | 9/2007 | Condie | |
| 2007/0293899 A1 * | 12/2007 | Sheldon et al. | 607/9 |
| 2008/0109041 A1 | 5/2008 | de Voir | |
| 2009/0088814 A1 * | 4/2009 | Good et al. | 607/25 |
| 2009/0234412 A1 * | 9/2009 | Sambelashvili | 607/25 |
| 2009/0275998 A1 * | 11/2009 | Burnes et al. | 607/4 |

FOREIGN PATENT DOCUMENTS

| | | |
|---|---|---|
| EP | 0624386 | 11/1994 |
| EP | 0830877 | 3/1998 |
| EP | 1302215 | 7/2004 |
| EP | 1449562 | 8/2004 |
| WO | WO 95/32758 | 12/1995 |
| WO | WO 02/051499 | 7/2002 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |
| WO | WO 2007/090003 | 8/2007 |

OTHER PUBLICATIONS (PCT/US2010/025566) PCT Notification of Transmittal of the International Search Report and the Written Opinion of the International Searching Authority.

M. Sweeney et al., "Multicenter, Prospective, Randomized Safety and Efficacy Study of a New Atrial-Based Managed Ventricular Pacing Mode (MVP) in Dual Chamber ICDs"; Journal of Cardiovascular Electrophysiology; vol. 16, No. 8, Aug. 1, 2005, pp. 811-817.

M. Sweeney et al., "Severe Atrioventricular Decoupling, Uncoupling, and Ventriculoatrial Coupling During Enhanced Atrial Pacing: Incidence, Mechanisms, and Implications for Minimizing Right Ventricular Pacing in ICD Patients"; Journal of Cardiovascular Electrophysiology Journal of Cardiovascular Electrophysiology; vol. 19, No. 11. Jun. 28, 2008, pp. 1175-1180.

* cited by examiner

SYSTEM AND METHOD FOR CONDITIONAL BIVENTRICULAR PACING

RELATED APPLICATION

The present application claims priority and other benefits from U.S. Provisional Patent Application Ser. No. 61/156,177, filed Feb. 27, 2009, entitled "A SYSTEM AND METHOD FOR CONDITIONAL BIVENTRICULAR PACING, incorporated herein by reference in it's entirety.

FIELD OF THE INVENTION

The present disclosure relates to implantable medical devices and more particularly, implantable medical devices that provide biventricular pacing.

BACKGROUND

Description of the Related Art

Implantable medical devices ("IMDs") provide various cardiac therapies including pacing, cardioversion and defibrillation. Initially, the primary purpose of a pacing therapy was to prevent symptomatic bradycardia due to disorders of impulse formation (i.e., sinus node dysfunction) or propagation (i.e., atrioventricular block).

Pacing systems evolved with the goal of providing full control of the electrical timing of the heart in order to more closely mimic the precise electromechanical relationships of the cardiac cycle. For example, in a conventional dual chamber pacing system (right atrial (RA) and right ventricular (RV) pacing), a dual chamber pacing mode such as DDD/R could provide atrial timing to control heart rate in response to sensed physiological demand (i.e., increasing or decreasing heart rate as needed) and provide properly timed atrial-synchronous RV pacing to assure atrioventricular (AV) synchrony. In this manner, the various timing parameters were well defined and controlled. That is, the pacemaker AV delay (AVD: time from sensed or paced RA event to a RV paced event unless inhibited by a spontaneous ventricular event) was set to a physiologically desirable value that maximized ventricular pump function during systole and the corresponding ventriculo-atrial (VA) interval was sufficiently long to permit ventricular relaxation and filling during diastole. In general, the implantation of a dual chamber device is relatively straightforward and the implementation and operation of such a conventional device in a dual chamber mode (e.g., DDD, DDD/R, etc.) became a gold standard for therapy.

Awareness of the detrimental effects of electrical timing disturbances on cardiac pump function encouraged the use of multisite pacing stimulation as electrical therapy for other types of cardiac disease. As an example, many systolic heart failure patients with intact AV conduction and proper intrinsic rate control also have ventricular conduction disturbances which cause regional mechanical delay (contraction asynchrony) that worsens pump function. Cardiac resynchronization therapy (CRT) was developed to provide pacing stimuli to both the RV and left ventricle (LV) (and typically the RA) to restore and maintain AV synchrony similar to conventional dual chamber pacemakers, and additionally, to restore and maintain ventricular contraction synchrony using biventricular (RV+LV) stimulation techniques. CRT is an important and established therapy for systolic heart failure accompanied by ventricular conduction delay resulting in LV contraction asynchrony.

Any technique of biventricular pacing requires delivery of a specially designed pacing lead to the epicardial or endocardial surface of the LV. This can be achieved by several different approaches, including transvenous epicardial, transvenous endocardial and direct epicardial via limited left lateral thoracotomy. Generally, LV pacing leads are delivered transvenously to the RA, navigated through the coronary sinus into a coronary vein tributary adjacent an exterior portion (epicardial surface) of the LV. Currently, application of biventricular pacing is confined to patients with systolic heart failure and ventricular conduction delay that occurs spontaneously or is imposed by obligatory RV pacing.

Conventional dual chamber pacing prioritizes AV timing by synchronizing a RV paced beat to every RA event (paced or sensed), even when AV conduction is intact. Over time, there has been recognition in the field that RV apical (RVA) pacing (i.e., only providing ventricular pacing in the right ventricular apex), despite maintenance of AV synchrony, is associated with increased risks of atrial fibrillation, heart failure and death. These adverse effects are attributed to disruptions to AV timing and an asynchronous ventricular contraction sequence obligated by RVA-only pacing. In many patients obligatory RVA-pacing is a consequence of inviolable pacemaker timing rules. Consequently, new pacemaker modes were developed to prioritize intrinsic AV conduction and spare RVA pacing, permitting significantly prolonged AV conduction times and occasional missed ventricular beats.

Accordingly, a pacing protocol to promote intrinsic conduction has been developed having a protocol that is commercialized in various embodiments as MVP™ (Managed Ventricular Pacing™). In summary, MVP™ operates to provide a pacing protocol that provides multiple-beat AV synchronization and minimizes or reduces RV pacing by (1) eliminating the pacemaker AV interval (AVI) and restrictions on the PR interval and (2) occasionally tolerating a complete cardiac cycle devoid of ventricular activity while prioritizing intrinsic AV conduction and ventricular contraction synchrony. In other words, the protocol tolerates a complete cardiac cycle devoid of ventricular activity (i.e., no sensed spontaneous ventricular event, no ventricular pacing) while providing properly timed atrial synchronous ventricular pacing in the cycle immediately subsequent to the cardiac cycle devoid of spontaneous ventricular activity. If there is a loss of intrinsic conduction for a prolonged period of time, the protocol will cause the device to operate in a dual chamber mode (e.g., DDD/R) to maintain AV synchrony and prevent ventricular asystole, and to periodically perform conduction checks for recovery of intrinsic AV conduction. Minimization of unnecessary RVA pacing using such techniques has been shown to reduce the risks of atrial fibrillation and heart failure compared to obligatory RVA pacing at standard AV delay settings associated with conventional dual chamber pacemakers.

While these kinds of pacing protocols provide ever safer and efficacious therapies for various patient populations, there remain numerous other patient populations that lack an effective pacing therapy to address their cardiac condition.

DETAILED DESCRIPTION

Figure 1:
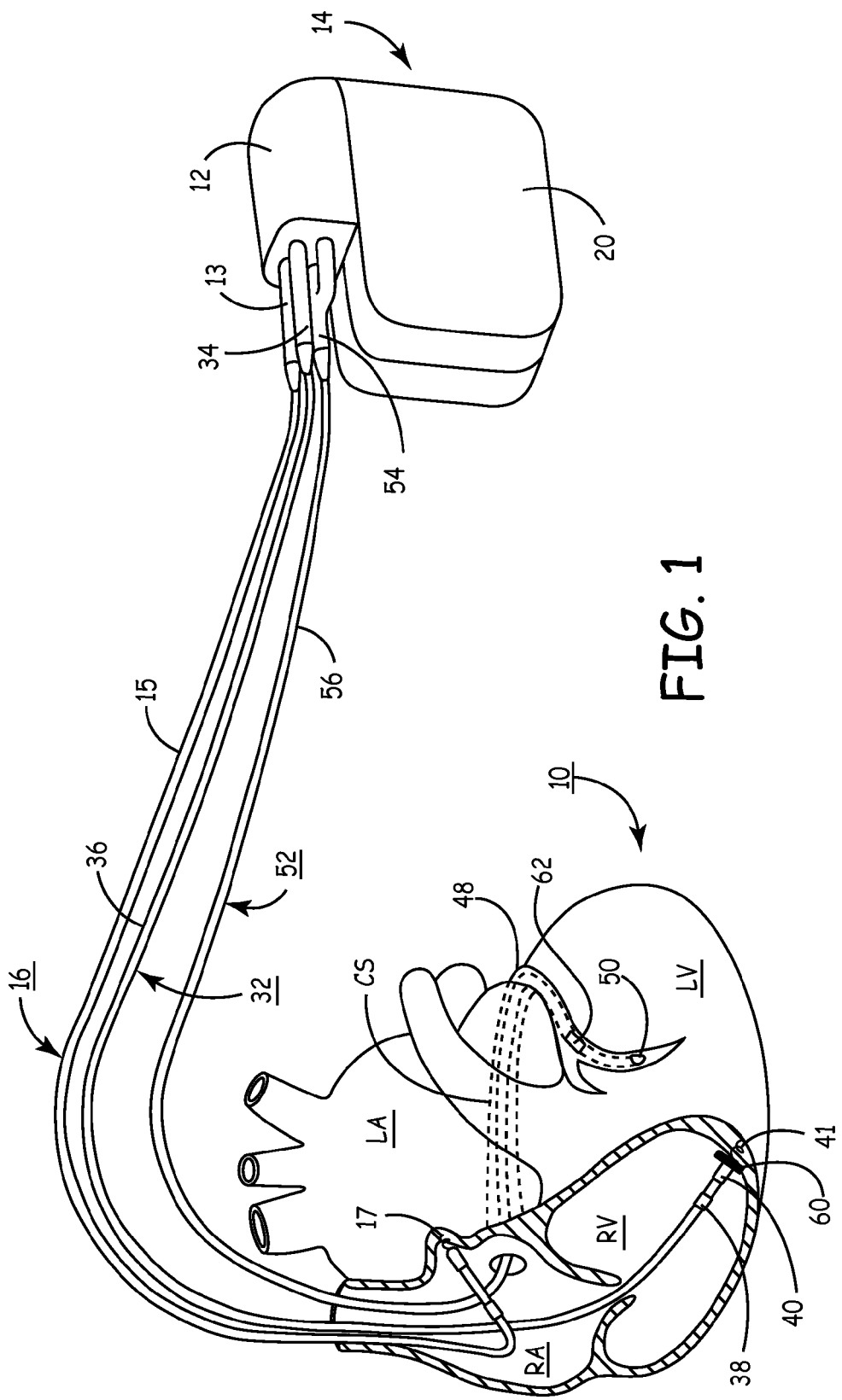
FIG. 1 is an illustration of an implantable pulse generator configured for biventricular pacing.

FIG. 1 depicts an implantable medical device (IMD) embodied as a multi-chamber cardiac pacemaker or implantable pulse generator (IPG) 14. While an IPG is illustrated, it will be appreciated that embodiments may be provided that include and implantable cardioverter defibrillator (ICD) having pacing capabilities. The multi-chamber IPG 14 is configured to deliver pacing pulses to one or more heart chambers as needed to control the heart activation sequence or provide other therapy. The IPG 14 is shown in communication with patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) extending from the opening in the right atrium laterally around the atria to form the great cardiac vein 48, which branches to form inferior cardiac veins.

The IPG 14 is typically implanted subcutaneously in a patient's body between the skin and the ribs. The transvenous endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of connector block 12 that is coupled to a pair of electrically insulated conductors within lead body 15 and connected with distal tip RA pace/sense electrode 19 and proximal ring RA pace/sense electrode 21 provided for achieving RA pacing and sensing of RA electrogram (EGM) signals.

Bipolar, endocardial RV lead 32 is passed through the RA into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals. RV lead 32 further includes an RV wall motion sensor 60. RV wall motion sensor 60 may be positioned into or proximate the RV apex for detecting motion or acceleration of the RV apical region. Implantation of an acceleration sensor in the right ventricle is generally disclosed in U.S. Pat. No. 5,693,075 issued to Plicchi, et al., incorporated herein by reference in its entirety.

In this illustrated embodiment, a unipolar, endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of connector block 12. A small diameter unipolar lead body 56 is selected in order to lodge the distal LV CS pace/sense electrode 50 deeply in a cardiac vein branching from the great cardiac vein 48.

Coronary sinus lead 52 may optionally be provided with a wall motion sensor 62 capable of generating a signal proportional to the acceleration of the left ventricular free wall.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductor extending proximally from the more proximal LA CS pace/sense electrode(s) and terminating in a bipolar connector 54.

Figure 2:
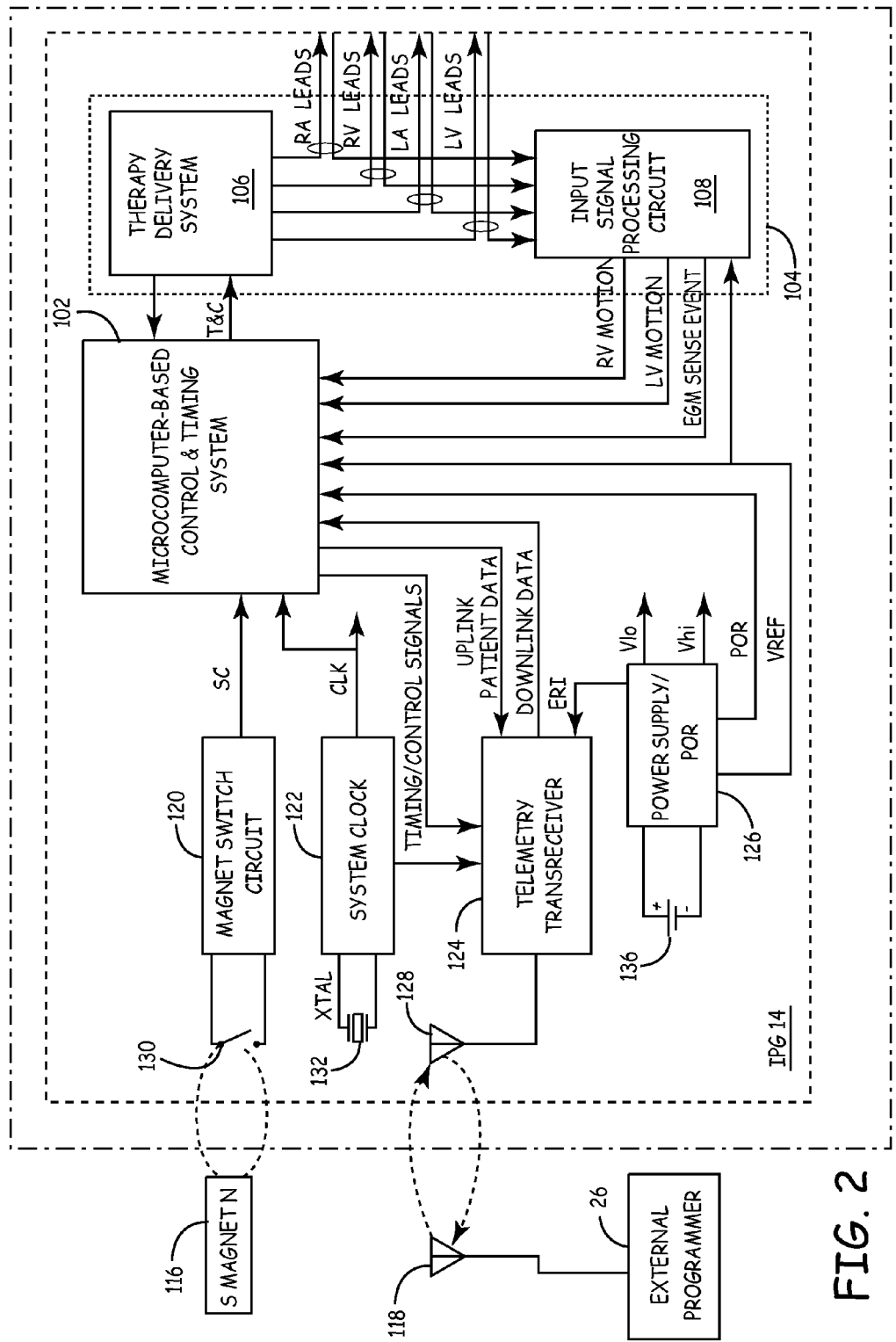
FIG. 2 is a schematic block diagram of an exemplary multi-chamber pacemaker or implantable pulse generator (IPG), such as that shown in FIG. 1.

FIG. 2 is a schematic block diagram of an exemplary multi-chamber IPG 14, such as that shown in FIG. 1, that provides bi-ventricular or triple chamber pacing. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize heart chamber activation. The interface circuitry 104 therefore includes a therapy delivery system 106 intended for delivering cardiac pacing impulses under the control of control and timing system 102. Delivery of pacing pulses to two or more heart chambers is controlled in part by the selection of programmable pacing intervals, which can include atrial-atrial (A-A), atrial-ventricular (A-V), and ventricular-ventricular (V-V) intervals.

Physiologic input signal processing circuit 108 is provided for receiving cardiac electrogram (EGM) signals for determining a patient's heart rhythm. Physiologic input signal processing circuit 108 additionally receives signals from left ventricular wall acceleration sensor 62, and RV wall acceleration sensor 60, and processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV.

Control and timing system 102 controls the delivery of bi-atrial, bi-ventricular, or multi-chamber cardiac pacing pulses at selected intervals intended to improve heart chamber synchrony. The delivery of pacing pulses by IPG 14 may be provided according to programmable pacing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine.

The therapy delivery system 106 can optionally be configured to include circuitry for delivering cardioversion/defibrillation therapy in addition to cardiac pacing pulses for controlling a patient's heart rhythm. Accordingly, leads in communication with the patient's heart could additionally include high-voltage cardioversion or defibrillation shock electrodes.

A battery 136 provides a source of electrical energy to power components and circuitry of IPG 14 and provide electrical stimulation energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. Not all of the conventional interconnections of these voltages and signals are shown in FIG. 2.

Current electronic multi-chamber IPG circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data, including acceleration data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or LV acceleration data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 includes electrical signal amplifier circuits for amplifying, processing and sensing events from characteristics of the electrical sense signals or sensor output signals. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an atrial sense or ventricular sense event signal to the control and timing system 102. Timing and control system 102 responds in accordance with its particular operating system to deliver or modify a pacing therapy, if appropriate, or to accumulate data for uplink telemetry transmission in a variety of ways known in the art. Thus the need for pacing pulse delivery is determined based on EGM signal input according to the particular operating mode in effect.

As previously discussed, biventricular pacing may be provided as a therapy in the form of CRT (cardiac resynchronization therapy) for heart failure patients having ventricular contraction asynchrony due to conduction disturbances. This does not address the substantial class of patients who have systolic heart failure, normal ventricular conduction and contractile synchrony, generally intact AV conduction, but with varying degrees of prolonged PR intervals, which may degrade LV pump function. For this group of patients, dual chamber pacing may be provided, but as indicated, typically results in a very high percentage of RVA pacing which is associated with increased risks of heart failure and death. Alternatively, a dual chamber device using a protocol such as MVP™, which promotes intrinsic conduction, would minimize potentially adverse RVA pacing, but would not correct spontaneously prolonged PR intervals and may worsen or induce long PR intervals during desired or necessary atrial pacing (collective referred to as AV desynchronopathy). This may be particularly problematic for patients who require frequent, or continuous, atrial pacing support due to sinus node dysfunction that occurs spontaneously, or due to necessary cardiovascular medications As used herein, the term AV interval (atrial-ventricular interval) or AVI means an estimate by the implantable medical device of the physiologic PR interval as initiated by either an intrinsic RA depolarization or RA pacing pulse, as measured from the sensed (or the known timing of the paced) atrial activation to the resulting spontaneous RV sensed event.

As used herein, the term minimal biventricular pacing mode (MBVP) means a pacing protocol or pacing mode that:
  operates in an atrial based pacing mode providing RA pacing while monitoring for RV sensed events, wherein biventricular pacing is precluded while operating in the atrial based pacing mode;
  permits a complete cardiac cycle defined by an A-A interval to lapse without a RV-sensed event;
  provides a back-up biventricular pacing in an A-A interval immediately subsequent to an A-A interval devoid of a RV-sensed event, wherein the backup biventricular pacing pulse is synchronized to the atrial event initiating the A-A interval in which the back-up is provided; and
  operates in a triple chamber pacing mode if a predetermined number of cardiac cycles are devoid of RV-sensed events, wherein the triple chamber pacing mode provides biventricular pacing in each cardiac cycle unless inhibited.

Minimal biventricular pacing (MBVP) may be a discrete pacing mode or may be an overarching protocol that causes mode changes to achieve a prescribed effect. In MBVP, rather than just providing a RV pacing pulse when ventricular pacing is required, properly timed biventricular pacing is provided in response to certain conditions indicated by analysis of the occurrence/non-occurrence of intrinsic AV conduction in each cardiac cycle, described below in reference to FIGS. 3A and 3B. Thus, all of the variations and attributes described with reference to the RV mode are similarly available in the biventricular version as are the various programmable attributes of biventricular pacing (e.g., sequential RV-LV timing). Finally, it will be appreciated that in some instances, the biventricular version may provide monochamber (i.e., RV- or LV-only) pacing. Reasons may include damage to a ventricular lead, physiological impairment (e.g., loss of monochamber capture), or physician preference.

As used herein, the term AV-DC (AV decoupling) means delayed AV coupling, indicated by AVIs that exceed a predetermined acceptable value and resulting in AV desynchronization, which may adversely affect ventricular pump function.

As used herein, the term AV-UC (AV uncoupling) means a transient or permanent breakdown in 1:1 AV conduction (e.g., heart block).

As used herein, the term VA-C (VA coupling) means ventriculo-atrial association, indicated by a VA interval that is less than a predetermined value, and possibly resulting in reduced ventricular preload or atrial transport block, collectively referred to as the "pseudo-pacemaker syndrome".

It is therefore understood that AV-DC, VA-C and AV-UC represent a time continuum of progressively increasing AV conduction time to the point of conduction failure.

Figure 3A:
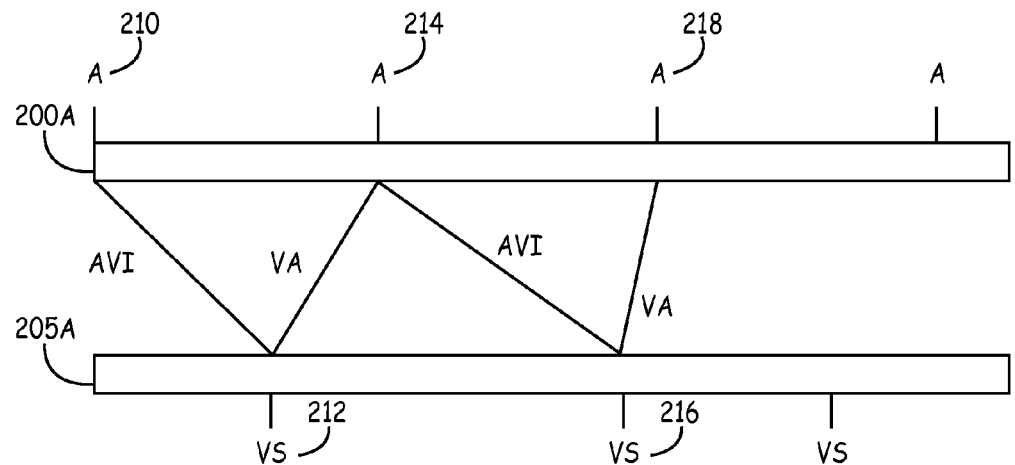
FIGS. 3A and 3B are timing diagrams illustrating a series of cardiac cycles.

FIG. 3A illustrates a timing diagram of operation in the MBVP mode, with bar 200A representing an atrial channel and bar 205A representing a ventricular channel. Each "A" on the atrial channel 200 represents a RA event (paced or sensed) that initiates depolarization of the heart and the cardiac electromechanical cycle. Each subsequent A terminates the current cardiac cycle and initiates the next cardiac cycle. Thus, as used herein, a cardiac cycle is defined as an A-A interval.

In MBVP, the normal condition is to operate in an atrial based pacing modality such that RApacing is provided according to the normal operating parameters. For a given cycle operating in this modality, ventricular pacing is precluded. Thus, in FIG. 3A, the initial RAevent 210 occurs and is followed in time by a sensed (intrinsically conducted) RVevent 212. The time interval between the RAevent 210 and sensed RV event 212 is denoted as the (pacemaker) AVI. This is a measured time interval and this term (AVI) is used differently here than may be commonly seen elsewhere. Specifically, in other contexts the term AVI may be used to designate a timer that is initiated with an atrial event and upon expiration of the timer a scheduled ventricular pacing pulse. For clarity, applicant will use the term paced AV delay (PAVd) to designate a timer that will end in a ventricular pacing pulse (if not inhibited).

As indicated, when the RVevent 212 is sensed, it completes the measurement of the pacemaker AVI, which is therefore an estimate of the patient's physiologic PR interval. The time interval between the RV sensed event 212 and the subsequent RA event 214 is referred to as the VA interval.

With MBVP, as long as there was a RVsensed event in the previous cardiac cycle, ventricular pacing is inhibited in the current cardiac cycle. Thus, in the second cardiac cycle illustrated in FIG. 3A, the AVI between RAevent 214 and RV sensed event 216 is considerably longer and represents a long PR interval (AV-DC). Consequently, the VA interval is very short. Nonetheless, intrinsic AV conduction is present and the MBVP mode continues to operate normally.

Figure 3B:
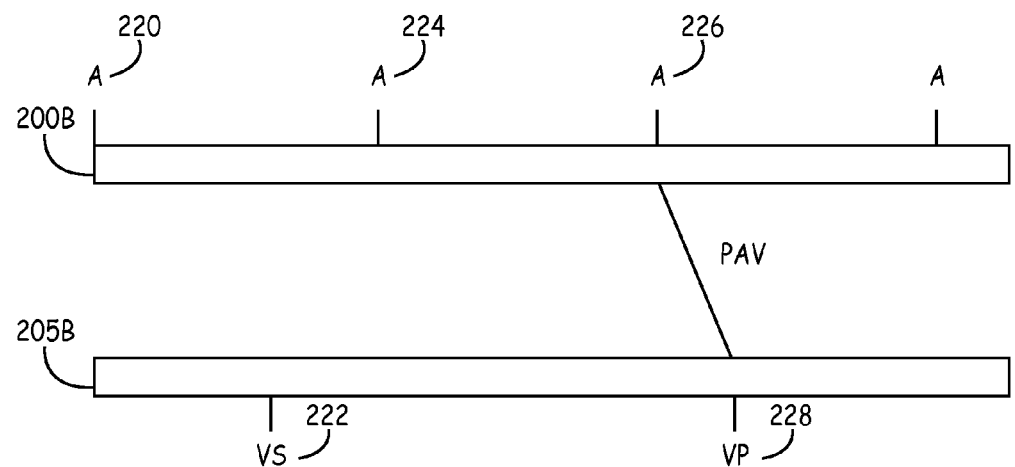

FIG. 3B illustrates operation of the MBVP mode when a cardiac cycle is devoid of a RV-sensed event. A RA event 220 occurs and is followed by a RV-sensed event 222, which therefore precludes ventricular pacing in the subsequent cardiac cycle, which is initiated by a RA event 224. As illustrated, the entire A-A interval (A 224 to A 226) is devoid of any sensed ventricular activity. In the third cardiac cycle, the MBVP mode initiates a PAVd timer upon commencement of the atrial event 226. At the expiration of the PAVd, a ventricular pacing pulse 228 is delivered. This protocol promotes intrinsic AV conduction by allowing for the maximum amount of time in a given cycle for intrinsic AV conduction to occur. In this manner, intrinsic AV and ventricular conduction are prioritized despite the occurrence of an occasional missed ventricular event.

While not illustrated, MBVP would generally preclude ventricular pacing in the next sequential cardiac cycle after a single ventricular pacing pulse. Therefore, if the first nonconducted atrial cycle marks the onset of persistent heart block, the effective ventricular rate would be halved unless additional ventricular pacing were provided. Thus, MBVP monitors overall conduction and if a predetermined number of cardiac cycles are devoid of ventricular activity over a given span (e.g., 2 of 4 contiguous cycles), then a mode change is effected to provide more robust atrial-synchronous ventricular pacing (e.g., a DDD-like mode, where ventricular stimulation is delivered in a biventricular configuration).

Thus, MBVP provides the benefit of promoting intrinsic conduction while offering back up biventricular pacing as required, and has the ability to determine when more robust ventricular pacing is required.

On the other hand, by virtue of providing the entire cardiac cycle for intrinsic conduction to emerge, the protocol will permit or induce long AVIs (e.g., as illustrated in the A-A interval initiated by atrial event 214). As previously discussed, this condition is referred to as AV-DC, which may degrade LV pump function over time, particularly in patients with systolic heart failure. There is not a currently accepted clinical value for what constitutes an AVI that is "too long" in the context of otherwise obligatory RVA pacing, however, the range of normal PR intervals is well-known. Thus, the value will be provided as a programmable parameter. Spurious or infrequent cycles having long AVIs, while relevant as data points for evaluating AVI behavior, are not the primary concern. Rather, the patient's overall burden of long AVIs is important; thus, it is percentage of time that the patient has long AVIs that is most relevant and targeted for therapy.

Furthermore, there is often a correlation between long AVIs (and corresponding PR intervals) and other predictable and recurrent physiologic circumstances. AVIs are known to be consistently longer during conditions of atrial pacing versus sinus rhythm, and this increase in AVI duration is known to be 50-100 milliseconds (ms). In either situation of sinus rhythm or atrial pacing, AVIs are further susceptible to prolongation due to increasing heart rates and autonomic influences. For example, long AVIs may occur exclusively during sleep due to increased atrial pacing frequency and delayed AV conduction time attributable to changes in autonomic tone. Long AVIs may also occur during exercise due to physiologically delayed AV conduction at higher heart rates, and the latter may be aggravated by a desire for rate-modulated pacing. Consequently, AV-DC may be present only during conditions of atrial pacing, and absent during sinus rhythm.

Finally, undesirably slow ventricular rates may arise during atrial fibrillation, when no ordered relationship exists between atrial and ventricular contraction, a form of instantaneous AV-UC not due to true AV conduction failure (such as heart block, for example)

To address these issues, a novel pacing modality is provided that is referred to as conditional triple chamber pacing (CTCP).

Overview of CTCP-MBVP Integration

As used herein, the terminology conditional triple chamber pacing (CTCP) mode means a pacing mode that provides atrial and biventricular pacing in the same manner and according to the same rules as a dual chamber pacing mode such as DDD, DDD/R, DDI, etc. except that biventricular pacing is provided instead of RV only pacing, and the frequency of biventricular pacing is conditional upon historical and real-time assessment of AVI behavior.

In the case of MBVP, the therapeutic goal is conditional "minimization" of ventricular pacing when AVIs are in a suitable range. By comparison, the therapeutic goal of CTCP is to force continuous ventricular pacing in order to correct abnormal AVI behavior (AV-DC and AV-UC). This is done using biventricular stimulation in order to mitigate ventricular desynchronization that otherwise would accompany RVA pacing in a conventional dual chamber pacing platform. In some patients, CTCP would be applied at low situational frequency (for example, sleep or exercise) but in other patients this might be provided on a continuous basis (for example, patients who present with AV-DC at baseline, or during necessary or desired atrial pacing for heart rate support). Therefore, MBVP is best described as a therapy for minimizing biventricular pacing, whereas CTCP is a therapy for minimizing AV-DC and normalizing AVIs by forcing biventricular pacing.

In summary, CTCP is provided in a device having atrial (or biatrial) pacing capabilities along with biventricular pacing capabilities (e.g., as illustrated in FIGS. 1 and 2). CTCP operates the device according to the MBVP protocol and additionally monitors AVI burden. If the AVI burden exceeds a threshold, CTCP provides biventricular pacing in each cardiac cycle for a period of time necessary to normalize AVIs and then attempts to revert to MBVP if and when the long AVI condition terminates.

Figure 4:
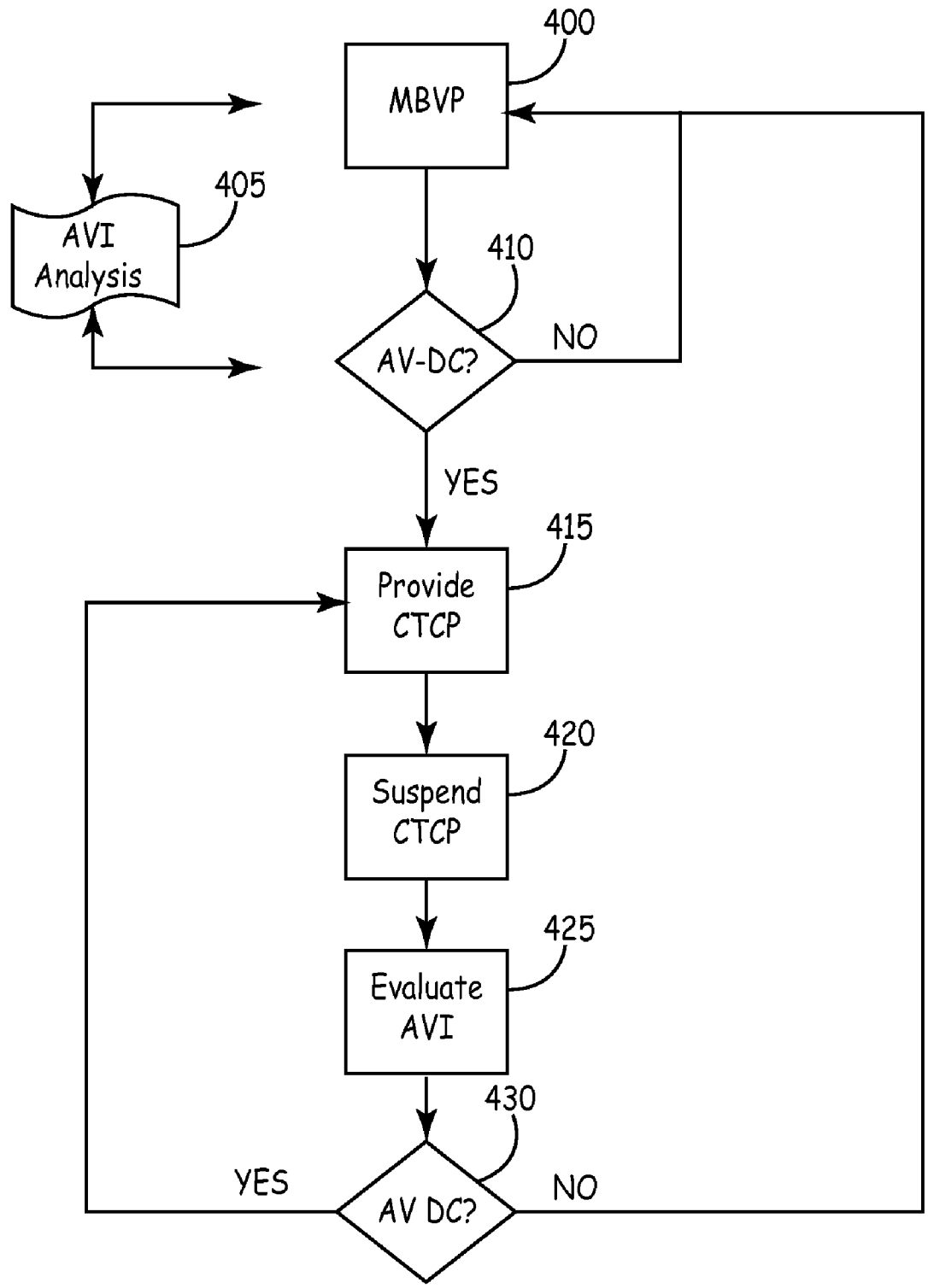
FIG. 4 is a flowchart describing a method of providing conditional triple chamber pacing, according to one embodiment.

A high level overview of CTCP is provided by the flowchart of FIG. 4. After establishing baseline AVI data for a given patient (to be described in greater detail below), the IPG 14 is programmed to operate (400) in the MBVP modality. The IPG 14 continues to monitor and collect (405) AVI data for each cardiac cycle. A determination is made (410) as to whether or not AV decoupling (AV-DC) has occurred. As indicated, this determination is preferably based upon physician programmed parameters. For example, the physician would select which AVI value (absolute magnitude in milliseconds of each timing interval per individual cardiac cycle) would be a threshold for AV-DC, and would likely select from values ranging from 200-450 ms in 10 ms increments. Then an overall burden threshold would be selected, indicative of a percentage of (1) time and/or (2) total cardiac cycles that the patient's AVI exceeds the numerical threshold. If the burden threshold exceeds this composite value, AV-DC is declared.

The importance of establishing an AVI burden threshold for declaring AV-DC is emphasized by AVI behavior in ambulatory ICD patients. High resolution cycle-by-cycle analysis obtained exclusively using investigational software tends to provide evidence that single time point measurements of AVIs are not robust estimators of lifetime AVI behavior. Statistical modeling indicates that, for example, a baseline PR interval of 240 ms does not guarantee that 100% of all AVIs will exceed 240 ms under any pacing condition. This apparent contradiction indicates that the baseline PR interval may overestimate the lifetime average AVI in some patients. Furthermore, the inaccuracy of a single AVI measurement for predicting lifetime average AVI behavior is modified by atrial pacing burden. For example, a baseline PR interval of 240 ms would require 80% cumulative atrial pacing to achieve a 90% probability of >40% all AVIs>250 ms; whereas a baseline PR interval of 300 ms would require about 30% cumulative atrial pacing to achieve a similar 90% probability of all AVIs>250 ms, despite the fact that baseline PR interval already exceeds the 250 ms threshold. From above, it must also be true that the baseline PR interval underestimates average AVI in some patients.

Therefore pacing therapy decisions for AVI management must be based on a cumulative assessment of AVIs (burden) reflecting varying physiologic and atrial pacing conditions, rather than a single baseline measurement or cycle-by-cycle measurement. This provides a critical distinction between the approach for determining AVI burden over time of the present disclosure, and the use of conventional AV delay hysteresis for treating AV-DC.

In the case of AV delay hysteresis, the pacemaker operates at 2 fixed AV delays, 1 long and 1 short. The AV delay (paced or sensed) is periodically increased from the shorter to the longer value. Occurrence of RV sensed events within the long AV delay inhibits ventricular pacing in accordance with conventional DDD timing rules. Occurrence of single, consecutive, or X of Y RV paced events at the long AV delay triggers reversion to the short AV delay. While this approach could be applied to correct AV-DC, it is heavily biased to ventricular pacing and would tend to overestimate the frequency occurrence of AV-DC since decisions to pace the ventricle are made on a cycle-by-cycle basis and without any acknowledgement of physiologic conditions (sleep, exercise, etc.) or circumstances invoking atrial pacing.

Since any form of ventricular pacing, including biventricular pacing, may induce contraction asynchrony and degrade LV pump function, CTCP should be provided only as needed based on an accurate historical and real-time assessment of AVI behavior, rather than AV hysteresis, to determine the true burden of AV-DC. In this manner, the present disclosure ensures that CTCP will be provided only as needed for situational AV-DC, thereby minimizing biventricular pacing whenever possible.

Figure 4A:
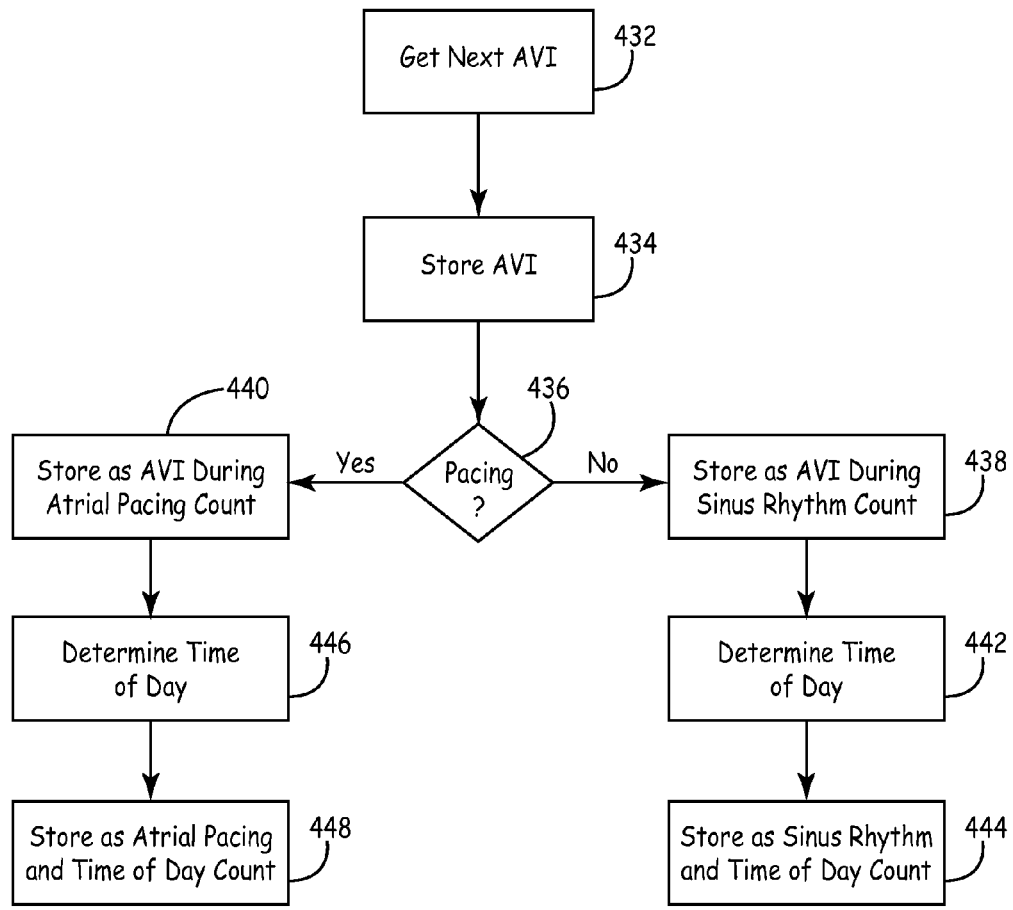
FIG. 4A is a flowchart illustrating an exemplary feature of cumulative assessment of AVI burden according to an embodiment of the disclosure.

FIG. 4A is a flowchart illustrating an exemplary feature of cumulative assessment of AVI burden according to an embodiment of the disclosure. An initial monitoring period of at least 24 hours would be used to establish the mean baseline AVI. This period is the minimum necessary to account for circadian variation in AVI behavior (encompassing at least 1 full wake-sleep cycle). AVIs will be recorded on every cardiac cycle (432) and stored (434). In one embodiment, the AVIs are placed in bins ranging 120-400 ms in 10-20 ms increments, for example. Since AVIs are expectedly longer during atrial pacing, separate counts will be maintained according to atrial pacing status. For example, if atrial pacing is not present (436), the AVI is stored and counted as having occurred during sinus rhythm (438), and if atrial pacing is present (436), the AVI is stored and counted as having occurred during atrial pacing (440). It is anticipated that the frequency of atrial pacing will be influenced by the interaction between prevailing sinus rates, lower programmed pacing rate, and the effects of circadian variation in autonomic effects throughout the course of a day.

In addition, the time of day associated with the occurrence of the AVIs occurring during normal sinus rhythm can be determined (442), so that each AVI is stored and counted as having occurred during sinus rhythm at a specified time of day (444). In the same way, the time of day associated with the occurrence of the AVIs occurring during atrial pacing can be determined (446), so that each AVI is stored and counted as having occurred during atrial pacing at a specified time of day (448). In one exemplary embodiment, including the specified time of day is used to distinguish between AVIs occurring during periods when it is likely the patient is awake and AVIs occurring during periods when it is likely the patient is asleep.

From this data, the AVIs will be calculated and reported as follows: (1) mean/median of all AVIs (all conditions of sensing or pacing) stored over the 24 hour monitoring period (434), (2) mean/median of the AVIs occurring during sinus rhythm only (438), (3) mean/median of the AVIs occurring during atrial pacing only (440), (4) mean/median of the AVIs occurring during sinus rhythm and during specific times of days, such as daytime vs. nighttime, where the time of day can be specified by the physician or set to nominal values, (5) mean/median of the AVIs occurring during atrial pacing during specific times of day, such as daytime vs. nighttime, where the time of day can be specified by the physician or set to nominal values that conform to the typical wake-sleep 24 hour cycle.

Based on clinical data derived from a large population of patients with systolic heart failure who received ICDs according to current evidence-based guidelines, had no ventricular conduction disturbance (i.e., no bundle branch block) and thus no indication for conventional CRT, and who were receiving good medical therapy, the minimum AVI threshold for AV-DC would be nominally set to 230 ms, for example. Therefore, if the baseline AVI monitoring period determines that $\leq 1\%$ of all AVIs are >230 ms, for example, CTCP will be withheld and a second AVI monitoring period will immediately be initiated. This monitoring period will be of greater duration (i.e., 7 consecutive days) and data output will be similarly composed. If $\leq 1\%$ of all AVIs remain >230 ms, serial 7 day monitoring periods will be schedule on monthly basis or, alternately, AVIs will be counted, classified and reported on a 30 day basis. It is understood that while the frequency count of AVIs under the 230 ms threshold is described as corresponding to 1%, other percentage values may be utilized as desired.

If it is determined that >1% of AVIs during any monitoring period exceeds 230 ms, a flag for AV-DC would be declared. The circumstances of AV-DC would be characterized (i.e., sinus rhythm, atrial pacing, time of day). The cumulative % time for AV-DC under each clinical condition will be reported. CTCP will be nominally invoked to continuously normalize AVIs at or exceeding 230 ms under any condition of sinus rhythm, atrial pacing, wake or sleep unless overridden by the physician. Flexibility in programming will permit selection of burden thresholds (defined as cumulative % time or cardiac cycles where AVI>230 ms).

It is expected that some patients will display AV-DC only under explicit, reproducibly recurring circumstances which provide additional opportunities for automaticity. For example, AV-DC occurring during atrial pacing at night could be addressed by triggering a sleep function to reduce the programmed atrial pacing rate by a selectable value in order to reduce pacing and reduce AV-DC burden. Similarly, AV-DC occurring only during rate responsive pacing could be addressed by automatically downregulating rate response parameters and reevaluating AVI behavior until AV-DC is eliminated.

It is also expected that some patients will have baseline AVI>230 ms at the time of implantation. In some patients this will be present during sinus rhythm at any heart rate due to severely impaired AV conduction. In other patients it will be present during continuous obligatory atrial pacing due to marked sinus bradycardia and a desire for physiologic heart rate. In either situation, CTCP will be invoked immediately upon termination of the initial monitoring period.

While the above determination is sufficient to determine AV-DC, CTCP in other embodiments uses additional criteria to define AV-DC, such as known and predictably recurring physiologic circumstances (i.e., sleep, exercise and atrial fibrillation). Thus, the IPG 14 may further discriminate AV-DC burden based upon these conditions. Sleep may be sensed or estimated. Accelerometers to determine position, activity, and breathing are known. Alternatively, time of day may be relied upon for an estimate of likely sleep pattern or the physician may input actual sleep times based on knowledge of the individual patient. Exercise and activity level can likewise be determined from accelerometers (e.g., demand pacing) or by monitoring intrinsic heart rates. Thus, the overall percentage required to determine AV-DC may be correlated to these activities rather than relying only a percentage of the total number of cardiac cycles. For example, using the above criteria, if more than 1% of cardiac cycles during periods of sleep include AVIs that exceed 230 ms, then AV-DC is identified. Assuming that the patient has shorter AVIs during waking hours, the threshold might not reach 1% of total time. Thus, by correlating the burden criteria to activities, it is possible to determine conditional AV-DC.

Returning to the flowchart of FIG. 4, the IPG 14 determines (410) whether or not AV-DC is present. If not, operation continues in MBVP (400). If AV-DC is present, the IPG 14 operates in the CTCP mode (415). In this manner, undesirably long AVIs are targeted for correction using biventricular pacing. This approach is intended to restore and maintain optimal physiologic AV synchrony while minimally disrupting LV contraction synchrony, unlike RVA pacing. CTCP would be maintained as long as AV-DC criteria were satisfied. If the patient were permanently in this status (long AVIs satisfying AV-DC criteria), then biventricular pacing would remain permanently enabled. In many or most cases however, the long AVIs are conditional; thus, there is a desire to revert to MBVP when possible. The IPG 14 will periodically suspend (420) CTCP (by reverting to MBVP and/or by providing progressively longer PAVd intervals) for a period of time and evaluate (425) the AVIs during the period of suspension to determine whether AV-DC is still present.

The evaluation during the suspension will require a number of cardiac cycles or time period to lapse to provide meaningful information. That is, following a period of biventricular pacing, return to baseline AV conduction may be delayed due to the residual effects of ventricular pacing or other autonomic perturbations. This could result in failure or delayed recognition of recovery of AV-C unless ventricular pacing is suspended for a sufficient period of observation. A gradual scheduled withdrawal of biventricular pacing may mitigate these residual effects on AV conduction and permit earlier recognition of AV coupling recovery. Searches for recovery of AV coupling (AV-C) may also be conditionally modified. For example, it is very likely that CTCP will be invoked during sleep and exercise but minimally at other times in many patients. Attempted withdrawal of CTCP during these conditions would be inappropriate. For example, a sufficiently long suspension during periods of sleep may be periodically performed to determine if the correlation continues over time. Alternatively, if a strong correlation exists, the IPG 14 may permanently correlate sleep with AV-DC and forego further attempts at suspending CTCP during periods of sleep. A strong correlation could be defined, for example, as >80% AVIs exceeding 230 ms during the observation period. Therefore, some conditions would provide for "permanent" but situation-specific application of CTCP.

If based upon the reassessment (425) of AVIs during the suspension, AV-DC persists, then CTCP is provided (415). If AV-DC is not detected (430) then the IPG 14 reverts to MBVP. Alternatively, reversion to MBVP may be based upon the termination of the correlative condition (e.g., sleep, exercise, atrial pacing) detected by alternate ongoing surveillance methods.

Figure 5:
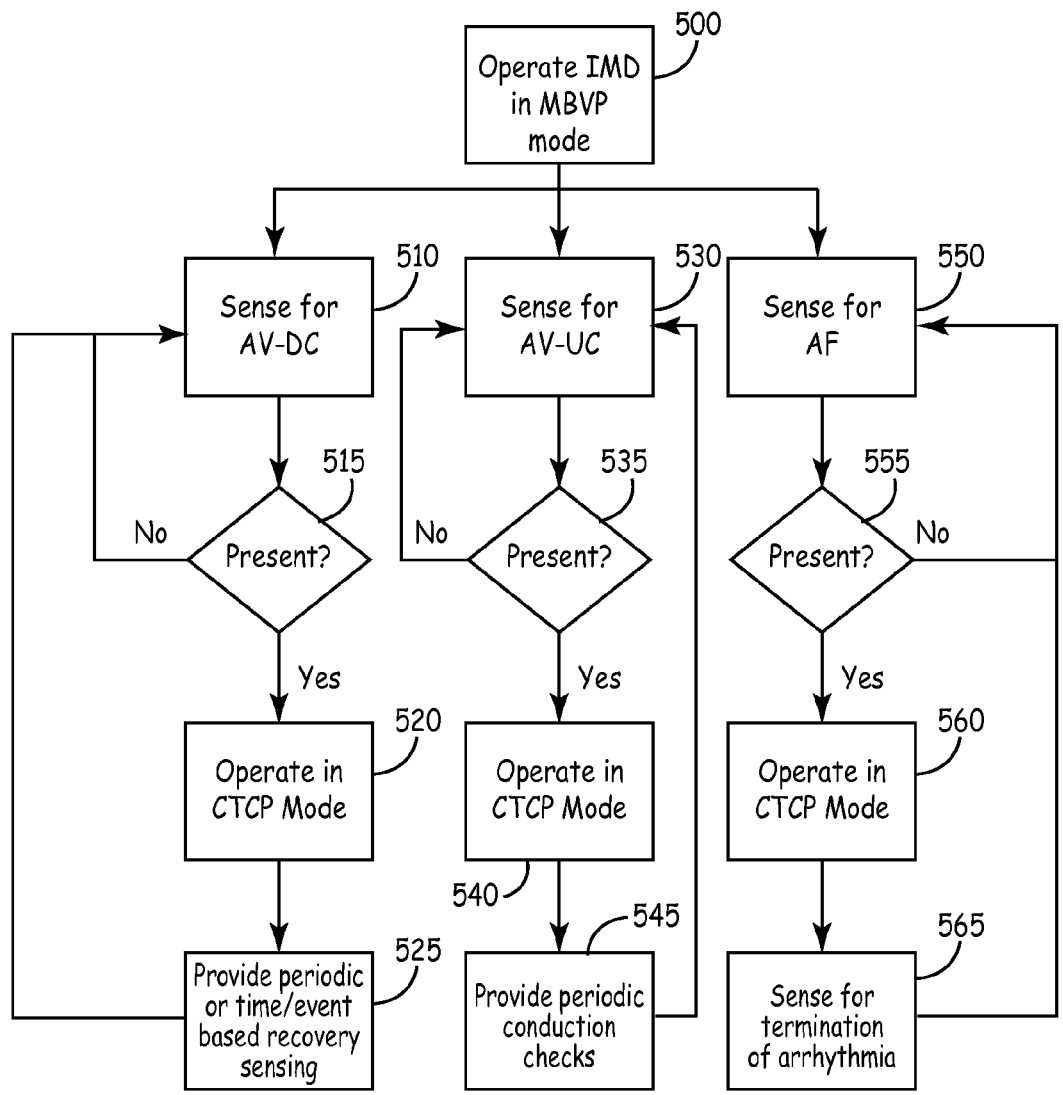
FIG. 5 is a flowchart describing three conditions sensed for during operation in conditional triple chamber pacing, according to one embodiment.

FIG. 5 is a high level overview of the application of CTCP according to an embodiment of the disclosure. As before, the IPG 14 (once initialized) operates (500) in an MBVP mode. During operation, the IPG 14 is sensing for three relevant conditions (in additional to normal operating parameters) that trigger CTCP. Specifically, the IPG 14 is sensing for AV-DC (510), AV-UC (530), and AF (550).

The IPG 14 determines (515) whether AV-DC is present and if not, continues in MBVP. If AV-DC is present, then the IPG 14 operates (520) in the CTCP mode, while periodically evaluating (525) whether AV-DC is still present (as described above).

The IPG 14 is also monitoring for AV-UC (transient or persistent breakdowns in AV conduction, i.e., heart block). If not present (535), operation of the device continues without ventricular pacing in the MBVP mode. If AV-UC occurs, then conditional triple chamber pacing (CTCP) (540) is provided, and the IPG 14 will periodically initiate conduction checks for resolution of AV-UC (1:1 AV conduction recovery) (545).

During AF surveillance, which occurs on a continuous basis, parallel to monitoring for AC-DC and AV-UC, if the IPG 14 determines (555) that AF is present and if ventricular rates are below the lower programmed pacing rate limit, then conditional triple chamber pacing (CTCP) is provided (560) until the AF is terminated (565).

In summary, the IPG 14 operates in the MBVP mode which is intended to minimize ventricular pacing. From this state, there are three conditions that will lead to intermittent and situational, or persistent biventricular pacing, each with its own set of controlling parameters. With AV-DC, CTCP provides atrial synchronous biventricular pacing in every cardiac cycle for a period of time in order to offset the burden of undesirably delayed AV conduction (long PR intervals). This arrangement restores and maintains optimally physiologic AV synchronization with biventricular pacing while minimizing LV contraction asynchrony, as compared to conventional RVA pacing. With AV-UC, biventricular pacing is continuously provided because intrinsic AV conduction has failed completely. CTCP is maintained until AV-UC has resolved or indefinitely if AV-C is not detected after a prescribed number of attempts or an absolute time has elapsed. During AF, AV-UC is instantaneous and AV-C cannot be restored until AF terminates. In the event of undesirably slow ventricular rates during AF, CTCP provides biventricular pacing to normalize heart rates while minimizing LV contraction asynchrony, as compared to conventional RVA pacing. It is further recognized that full recovery of AV-C may not occur when AV-UC or AF resolve. In some patients, the recovery state from AV-UC or AF will be AV-DC. When AV-DC is discovered upon resolution of AV-UC or AF, rules for managing AV-DC will be applied as previously outlined.

Figure 6:
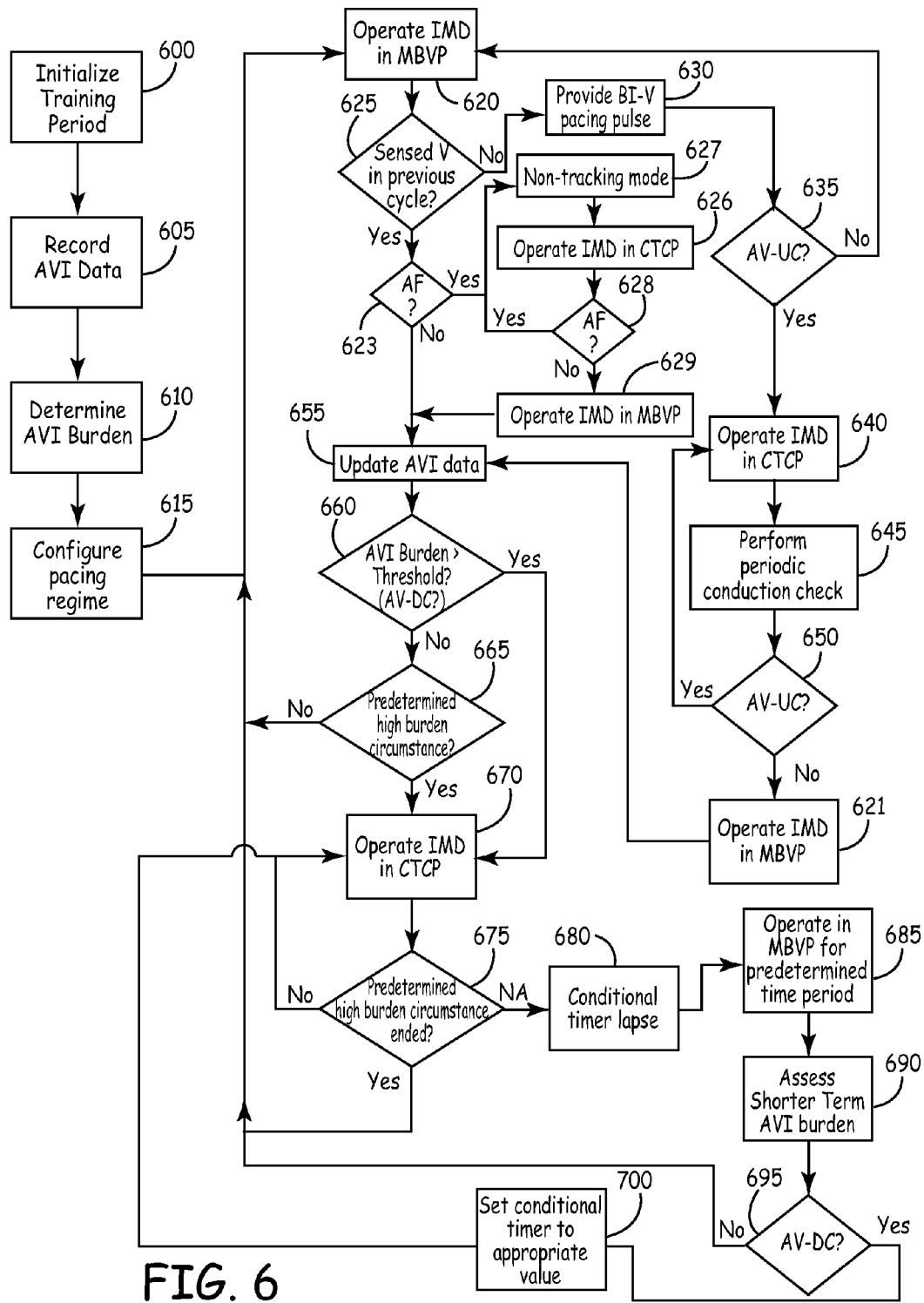
FIG. 6 is a flowchart describing a method of providing conditional triple chamber pacing according to one embodiment.

FIG. 6 is flowchart illustrating a more detailed CTCP protocol. In order to obtain baseline PR (AVI) data, an initial training period is provided (600), as described above. This may be conducted after the IPG 14 is implanted, but before any pacing therapies other than MBVP are initiated. The objective of the training period is to accurately characterize AVI behavior over a sufficient period of time on an individual patient basis in order to schedule CTCP in an appropriate manner. Further, in some embodiments, correlation may be made between AVI behavior and various high AV-DC or AV-UC burden circumstances such as atrial pacing, sleep, exercise, rate responsive pacing, AF or other conditions. Thus, the training period will increase progressively in scale over time.

As described above in reference to FIG. 4A, an initial monitoring period of at least 24 hours would be used to establish the mean baseline AVI. This period is the minimum necessary to account for circadian variation in AVI behavior (encompassing at least 1 full wake-sleep cycle). AVIs will be recorded on every cardiac cycle (432) and stored. In one embodiment, the AVIs are placed in bins ranging between 120-400 ms in 10-20 ms increments, for example. Since AVIs are expectedly longer during atrial pacing, separate counts will be maintained according to atrial pacing status. For example, if atrial pacing is not present (436), the AVI is stored and counted as having occurred during sinus rhythm (438), and if atrial pacing is present (436), the AVI is stored and counted as having occurred during atrial pacing (440). It is anticipated that the frequency of atrial pacing will be influenced by the interaction between prevailing sinus rates, lower programmed pacing rate, and the effects of circadian variation in autonomic effects throughout the course of a day.

In addition, the time of day associated with the occurrence of the AVIs occurring during normal sinus rhythm can be determined (442), so that each AVI is stored and counted as having occurred during sinus rhythm at a specified time of day (444). In the same way, the time of day associated with the occurrence of the AVIs occurring during atrial pacing can be determined (446), so that each AVI is stored and counted as having occurred during atrial pacing at a specified time of day (448). In one exemplary embodiment, including the specified time of day is used to distinguish between AVIs occurring during periods when it is likely the patient is awake and AVIs occurring during periods when it is likely the patient is asleep.

From this data, the AVIs will be calculated and reported as follows: (1) mean/median AVI (all conditions of sensing or pacing) stored over the 24 hour monitoring period (434), (2) mean/median of the AVIs occurring during sinus rhythm only (438), (3) mean/median of the AVIs occurring during atrial pacing only (440), (4) mean/median of the AVIs occurring during sinus rhythm only and during specific times of day, such as by daytime vs. nighttime, where the time of day can be specified by the physician or set to nominal values, (5) mean/median of the AVIs occurring during atrial pacing only and during specific times of day, such as by daytime vs. nighttime, where the time of day can be specified by the physician or set to nominal values that conform to the typical wake-sleep 24 hour cycle.

Additionally, a new training period could be automatically triggered by (1) a change in atrial pacing lower rate, (2) an observed increase in atrial pacing percentage, (3) an observed increase in back-up biventricular pacing during MBVP, (4) activation of a sleep program or entry of sleep/wake times via the user interface, (5) activation of rate modulation or during a programmer-based exercise response menu. Alternately, instead of relying upon the IPG 14 to conduct the training period, an external monitoring device (e.g., a Holter monitor with IPG real-time telemetry capabilities) may be utilized.

In any event, AVI data is recorded (605) for a period of time and the AVI burden is determined (610). In one embodiment, the IPG 14 bins data for predetermined AVI values (e.g., 100-150, 150-200 ms, etc) and keeps a count for each value range with respect to the total number of cycles on a rolling basis, tagged by rhythm status (sinus or atrial pacing), time of day, sensor input and other definable variables.

At the end of the training period, the CTCP pacing regimen is configured (615). This either means that the IPG 14 automatically configures parameters based upon AVI data collected during the start-up surveillance period or the physician programs values after reviewing data collected during the training period.

Based on clinical data derived from a large population of patients with systolic heart failure who received ICDs according to current evidence-based guidelines, had no ventricular conduction disturbance (i.e., no bundle branch block) and thus no indication for conventional CRT, and who were receiving good medical therapy, the minimum AVI threshold for AV-DC would be nominally set to 230 ms. Therefore, if the baseline AVI monitoring period determines that ≦1% all AVIs are >230 ms, CTCP will be withheld and a second AVI monitoring period will immediately be initiated. This monitoring period will be of greater duration (i.e., 7 consecutive days) and data output will be similarly composed. If <1% all AVIs remain >230 ms, serial 7 day monitoring periods will be scheduled on a monthly basis or, alternately, AVIs will be counted, classified and reported on a 30 day basis.

Alternately, the physician could select which AVI value (absolute magnitude in milliseconds of each timing interval per individual cardiac cycle) would be a threshold for AV DC, and would likely select from values ranging from 200, 250, 300, 350, 400, 450 ms or greater. Then an overall burden threshold would be selected, indicative of a percentage of (1) time and/or (2) total cardiac cycles that the patient's AVI exceeds the numerical threshold. If the burden threshold exceeds this composite value, AV-DC is declared.

Subsequent to training, the IPG 14 is configured to operate (620) according to an MBVP protocol. Thus, for a given cardiac cycle, the IPG 14 determines (625) whether there was a RV-sensed event in the immediately preceding cardiac cycle. If not, the IPG 14 provides (630) a properly timed ventricular pacing pulse. Next, the IPG determines (635) whether AV-UC is present or whether this was simply a single tolerable missed beat. For example, a determination is made as to how many recent cardiac cycles have been devoid of intrinsic ventricular activity. If the ratio of atrial to ventricular events exceeds 4:3, AV-UC is declared. Otherwise, persistent AV-UC is not identified (635) and operation returns to the atrial based mode of MBVP (620). If AV-UC is identified (635), then the IPG 14 operates (640) in the CTCP mode. At various times, the IPG 14 will perform (645) conduction checks to determine if intrinsic AV conduction has returned. Such a conduction check is performed by either gradually extending the PAVd or withholding ventricular pacing for a cardiac cycle. Such checks for return of conduction may be temporarily or permanently withheld when a sufficient history provides evidence that return of AV conduction is unlikely. After performing the conduction check, the IPG reevaluates (650) whether AV-UC is present. If it is, operation continues in the CTCP mode (640). If intrinsic conduction has returned and AV-C has been restored, the IPG resumes operation in the atrial based condition of MBVP (621). If intrinsic conduction has returned but remains impaired, satisfying criteria for AV-DC, the IPG continues in CTCP mode and, AVI data is updated (655) and AVI burden threshold for AV-DC is analyzed (660).

Likewise, if the IPG 14 determines (625) there was a sensed ventricular event in the immediately preceding cardiac cycle, the IPG 14 determines (623) whether AF is present. Analysis of atrial rhythm status occurs during all phases of operation. If AF is determined to be present, the IPG 14 switches (627) to a non-tracking mode (DDI/R) and, as long as the ventricular rate occurring during the determined AF is below the programmed rate, operates (626) in the CTCP mode. Since AF is an instantaneous form of AV-UC, no further analysis is needed and non-atrial synchronous biventricular pacing is provided based on analysis of intrinsic ventricular rate and/or sensor-indicated ventricular rate. In the event of undesirably slow ventricular rates during AF, CTCP provides biventricular pacing to normalize heart rates while minimizing LV contraction asynchrony, as compared to conventional RVA pacing. The IPG 14 determines (628) whether the AF has terminated, and once termination of AF is detected the IPG resumes operation in the atrial based condition of MBVP (629).

If intrinsic conduction is determined to be present (625), i.e., a ventricular event was sensed in the preceding cycle and if AF is not present (623) or has terminated, or once AV-UC is determined to no longer be present (650) during the conduction check (645), the IPG 14 updates (655) the AVI data. In one embodiment, the absolute magnitudes of the AVIs are stored as counts in the appropriate bins. Additionally, supplemental data indicating physiologic status and linked to AVI data such as atrial pacing percentage, time of day, estimates of sleep or wake, and parameters of exercise (rate response on, rate response level), etc., may also be stored.

With each additional data point, the IPG 14 evaluates (660) whether the threshold for AV-DC has been crossed. For example, if >1% of recent cardiac cycles have AVI>230 ms, then AV-DC may be declared. As indicated, the threshold percentage and interval durations may vary based upon clinical preference. If the threshold is crossed (660), then the IPG 14 operates (670) in the CTCP mode, wherein bi-ventricular pacing is provided (unless inhibited) in each cardiac cycle.

Even if the threshold has not been reached (660), the IPG 14 may switch to the CTCP mode (670) if a predetermined high burden circumstance is identified (665). That is, either during the testing period or over time, a correlation may be drawn between AVI behavior and various predictably recurring high AV-DC or AV-UC burden circumstances. Thus, rather than requiring the AV-DC burden to cross the threshold under these established circumstances, CTCP will be automatically applied without delay when such circumstances are recognized. As indicated, examples of such circumstances would be expected to include atrial pacing (particularly at high frequencies), sleep, exercise, or rate responsive pacing.

If >80% of all AVIs exceed 230 ms during any circumstance where alternate means of reducing AVIs are impractical (i.e., reducing atrial pacing rate), attempts to revert to MBVP could be suspended. On the other hand, situations where <80% of all AVIs exceed 230 ms could trigger attempts to revert to MBVP (620) when the high burden circumstance terminates (675). Alternatively, after a predetermined period of time (680), the IPG 14 reverts to MBVP (685) to determine whether or not AV-DC continues. Sufficient time is allowed to assess the return to normal of baseline timing of intrinsic conduction. This will likely be on the order of minutes and perhaps hours. If the IPG 14 determines the AV-DC is no longer present, the MBVP protocol is fully resumed (620). If AV-DC is present, then the conditional timer is reset (700) to an appropriate value and operation in the CTCP mode continues. In most circumstances, the duration of the conditional timer will be increased with each iteration.

Figure 7:
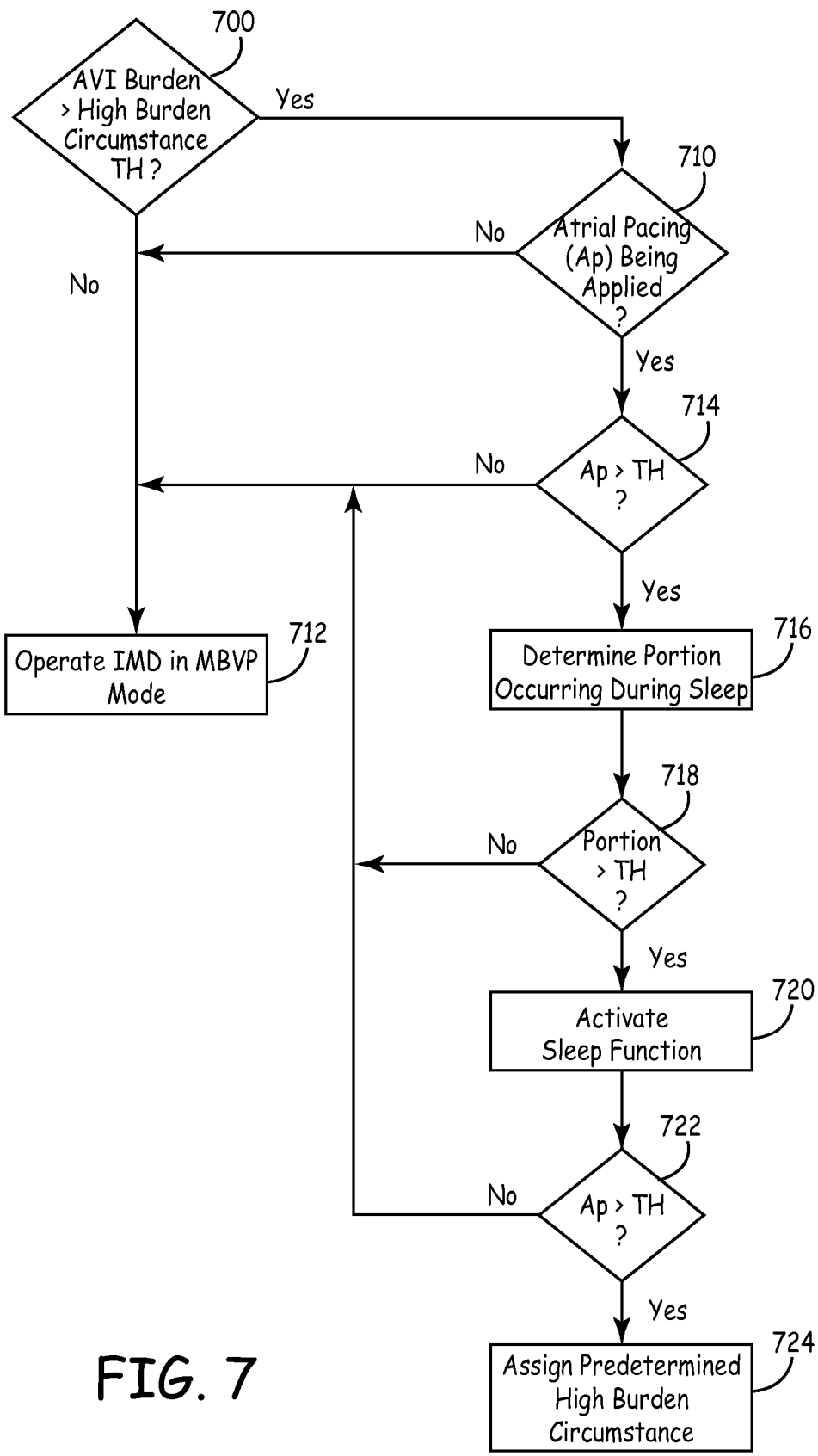
FIG. 7 is a flowchart illustrating an exemplary feature of cumulative assessment of AVI burden according to an embodiment of the disclosure.

FIG. 7 is a flowchart illustrating an exemplary feature of cumulative assessment of AVI burden according to an embodiment of the disclosure. During the initial training period, described above, recognition of certain interactions between bradycardia programming, AVIs, and intrinsic heart rate can be used to modify the CTCP operating hierarchy.

If the programmed bradycardia pacing rate substantially exceeds the patient's intrinsic heart rate, it is expected that atrial pacing will be delivered virtually 100% of the time. For example, if the prevailing sinus rate is 40 beats/minute and the lower pacing rate is programmed to 60 beats/minute, it is highly likely that atrial pacing will be delivered on every cardiac cycle. Thus, atrial pacing percentage will approach 100%, except under conditions where the patient's sinus rate exceeds the lower pacing rate, such as during exertion. Since exertional heart rates account for a minority (<1-5%) of total cardiac cycle time in the typical ambulatory device patient, the atrial pacing percentage will still approach 90-100%. This scenario is typically encountered in a patient with sinus node dysfunction, in whom a dual or multichamber ICD system was explicitly chosen to provide continuous physiologic heart rate support, in addition to other known and desired functions.

Therefore, if the AVI burden satisfies the AV-DC threshold, an assessment of atrial pacing percentage is made. If the atrial pacing percentage is sufficiently high, for example>80% (or other similarly appropriate thresholds), it is likely that (1) atrial pacing percentage will remain substantially high and (2) AV-DC will persist until the programmed atrial pacing rate is reduced. Consequently, further periodic assessments of AVI burden are unlikely to yield different results. Therefore, periodic determinations of the high burden circumstance are omitted, and the determination of a high burden circumstance would no longer be applicable for the patient. This status would remain indefinitely, unless the programmed atrial pacing rate was later reduced to a value at or below the prevailing sinus rate.

As described above, one of the high burden circumstances that may be identified as part of the cumulative AVI assessment of the present disclosure is the level of atrial pacing. It has been determined that, compared to patients who tend to receive substantially no atrial pacing therapy, those patients who receive substantial high level of atrial pacing therapy, but who do not reach the level of being identified as being continuously paced, were more likely to have an increased tendency towards experiencing heart failure. Therefore, according to an embodiment of the disclosure, during determination of high burden circumstances, if the patient was not previously identified during the training period as requiring delivery of a substantially continuous atrial pacing regimen to be delivered, the device determines whether the AVI burden is greater than a predetermined high burden circumstance threshold (700). In one embodiment, for example, the higher burden circumstance threshold is set as a percentage of AV intervals having a given length during a predetermined time period, such as 10 percent of the AVIs over a one week period that are greater than 230 ms, although greater AVI lengths, lengths of time and percentages may be utilized.

If the AVI burden is greater than the high burden circumstance threshold, i.e., greater than 10 percents of AVIs over a one week period are greater than 230 ms, a determination is made as to whether atrial pacing is being applied (710). If no atrial pacing is being applied, the high burden circumstance is not identified, and the device operates in the MBVP mode (712), described above. If atrial pacing is being applied, a determination is made as to whether the amount of atrial pacing that is being applied is greater than a pacing threshold (714). In one embodiment, the pacing threshold is set so that the determination in (714) includes determining whether atrial pacing is being applied more than 15 percent on an averaged daily basis. If the amount of atrial pacing being applied is not greater than the pacing threshold, i.e., 15 percent of the time on an averaged daily basis, the high burden circumstance is not identified, and the device operates in the MBVP mode (712), described above. If the amount of atrial pacing being applied is greater than the pacing threshold (714), a determination is made as to what portion of the atrial pacing is taking place during a predetermined condition (716), such as during sleep, for example. In another embodiment, the predetermined condition may be rate response, for example.

Once the portion of the atrial pacing taking place during the predetermined condition is determined, a determination is made as to whether the portion of the atrial pacing that is occurring during the predetermined condition is greater than a corresponding predetermined condition threshold (718). If the portion of the atrial pacing that is occurring during the predetermined condition is not greater than the predetermined condition threshold (718), the high burden circumstance is not identified, and the device operates in the MBVP mode (712), described above.

In an embodiment in which the predetermined condition is sleep, the determination in (718) includes determining whether the atrial pacing is being delivered while the patient is asleep. If atrial pacing is being delivered while the patient is asleep (718), a sleep function is activated (720). For example, activation of the sleep function includes lowering the pacing rate from the programmed rate to a lower rate. In one embodiment, the pacing rate is reduced from 60 bpm to 40 bpm. This sleep function remains activated for a predetermined period of time, such as one week for example. Once the sleep function has been activated for the predetermined period of time, a determination is made as to whether the amount of atrial pacing that is delivered during the sleep function is also greater than the atrial pacing threshold (722), i.e., more than 15 percent on an average daily basis.

If the amount of atrial pacing that is delivered is determined to be greater than the pacing threshold (722) despite activation of the sleep function, i.e., lowering of the pacing rate threshold, atrial pacing is determined to be a high burden circumstance (724), and the device operates in the CTCP mode whenever the high burden circumstance is determined to be taking place, i.e., when atrial pacing is being delivered. If the amount of atrial pacing that is delivered is determined not to be greater than the pacing threshold (722) during activation of the sleep function, the high burden circumstance is not identified, and the device operates in the MBVP mode (712), described above.

Figure 8:
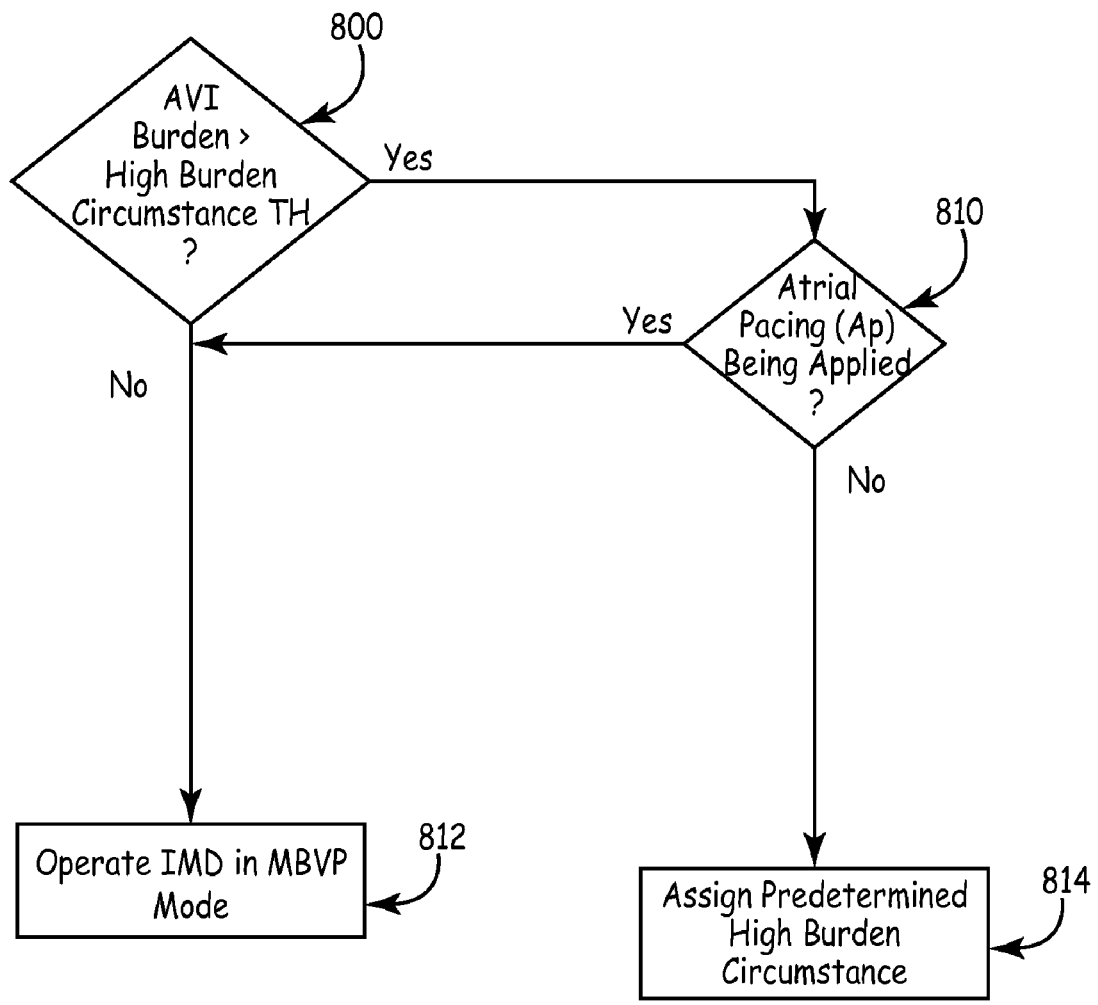
FIG. 8 is a flowchart illustrating an exemplary feature of cumulative assessment of AVI burden according to an embodiment of the disclosure.

FIG. 8 is a flowchart illustrating an exemplary feature of cumulative assessment of AVI burden according to an embodiment of the disclosure. Another potential high burden circumstance involves those patients who do not receive a substantial level of atrial pacing, but nonetheless tend to experience relatively prolonged spontaneous PR intervals, resulting in an increased tendency towards experiencing heart failure. Therefore, according to an embodiment of the disclosure, during determination of high AVI burden circumstances, a determination is made as to whether the AVI burden is greater than a predetermined high burden circumstance threshold (800). In one embodiment, the high burden circumstance threshold is set as greater than 10 percent of AVIs over a one week period being between 250 and 260 ms, for example. If the AVI burden is not greater than the high burden circumstance threshold, the high burden circumstance is not identified, and the device operates in the MBVP mode (812), described above.

If the AVI burden is greater than the high burden circumstance threshold, i.e., greater than 10 percent of AVIs over a one week period being between 250 and 260 ms a determination is made as to whether atrial pacing is being applied (810). In one embodiment, if the patient experiences less than 15 percent daily atrial pacing, the atrial pacing threshold is not satisfied and atrial pacing is determined to be not applied in (810). If atrial pacing is being applied, i.e., greater than 15 percent atrial pacing is being delivered daily, the high burden circumstance (no atrial pacing being delivered and AVI burden greater than 250 ms) is not identified, and the device operates in the MBVP mode (812), described above. If atrial pacing is not being applied, the high burden circumstance is assigned (814), and the device operates in the CTCP mode whenever the high burden circumstance is determined to be taking place, i.e., when no atrial pacing is being delivered and the AVI burden is greater than between 250-260 ms.

Figure 9:
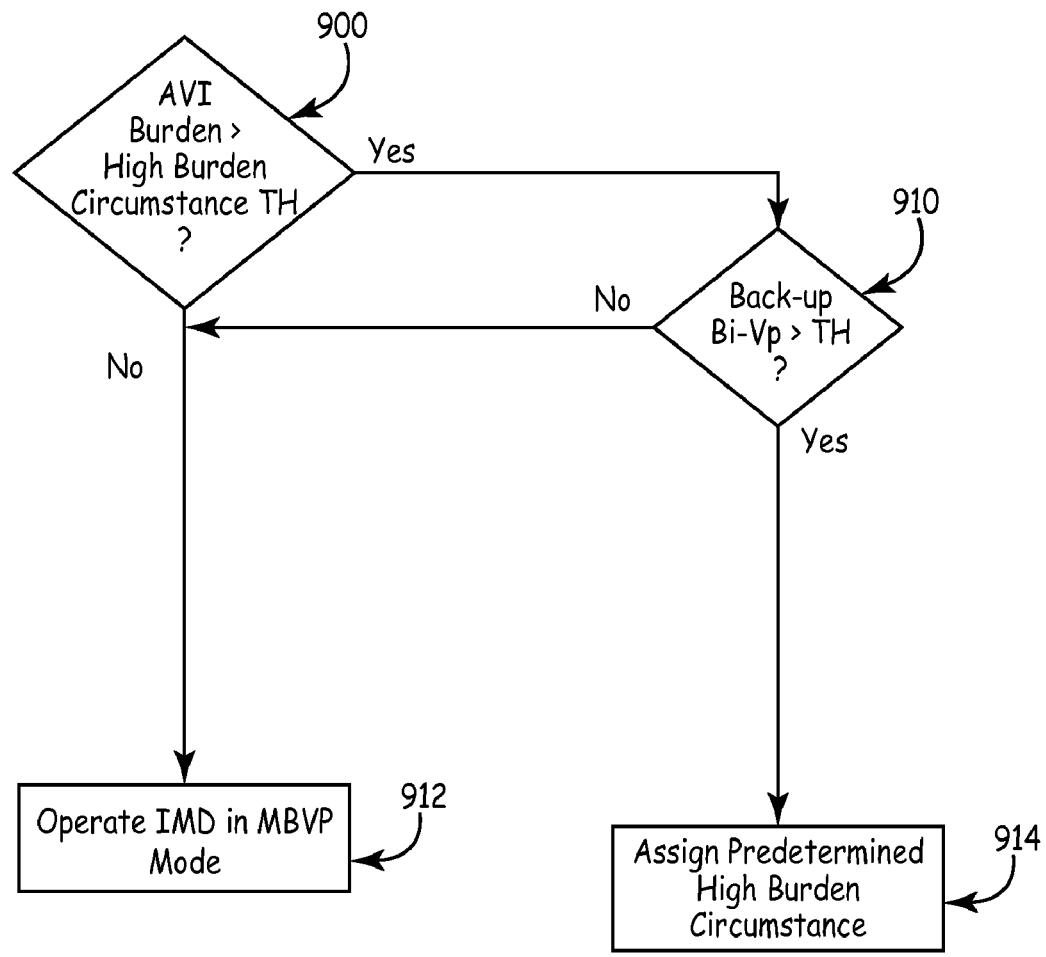
FIG. 9 is a flowchart illustrating an exemplary feature of cumulative assessment of AVI burden according to an embodiment of the disclosure.

FIG. 9 is a flowchart illustrating an exemplary feature of cumulative assessment of AVI burden according to an embodiment of the disclosure. Another potential high burden circumstance involves those patients who tend to experience relatively prolonged spontaneous PR intervals and experience a predetermined amount of back-up biventricular pacing (Bi-Vp) to be delivered while the device is in the MBVP mode. It has been found that worsening heart failure tends to result where AVIs are greater than 230 ms and this predetermined level of biventricular pacing being delivered for intermittent AV-DC is greater than between 10 and 15% during MBVP. Therefore, according to an embodiment of the disclosure, during determination of high AVI burden circumstances, a determination is made as to whether the AVI burden is greater than a predetermined high burden circumstance threshold (900). In one embodiment, the high burden circumstance threshold is set as a percentage of AV intervals having a given length during a predetermined time period, such as 10 percent of the AVIs over a one week period that are greater than 230 ms, for example, although greater AVI lengths, lengths of time and percentages may be utilized. If the AVI burden is not greater than the high burden circumstance threshold, the high burden circumstance is not identified, and the device operates in the MBVP mode (912), described above.

If the AVI burden is greater than the high burden circumstance threshold, i.e., 10 percent of the AVIs over a one week period being greater than 230 ms, a determination is made as to whether the amount of biventricular pacing that is being delivered when the device is in the MBVP mode is greater than a biventricular pacing threshold (912), i.e., greater than 10 to 15 percent biventricular pacing when in the MBVP mode, for example. If the amount of biventricular pacing that is being delivered is not greater than the biventricular pacing threshold, the high burden circumstance is not identified, and the device operates in the MBVP mode (912), described above. If the amount of biventricular pacing that is being delivered is greater than the biventricular pacing threshold, the high burden circumstance is assigned (914), and the device operates in the CTCP mode whenever the high burden circumstance is determined to be taking place, i.e., when AVI burden is greater than 230 ms and the amount of biventricular pacing being delivered when the device is in the MBVP mode is greater than between 10 and 15 percent.

Some of the techniques described above may be embodied as a computer-readable medium comprising instructions for a programmable processor such as a microprocessor, pacer/device timing circuit, or control circuit. The programmable processor may include one or more individual processors, which may act independently or in concert. A "computer-readable medium" includes but is not limited to any type of computer memory such as floppy disks, conventional hard disks, CD-ROMS, Flash ROMS, nonvolatile ROMS, RAM and a magnetic or optical storage medium. The medium may include instructions for causing a processor to perform any of the features described above for initiating a session of the escape rate variation according to the present invention.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. A medical device, comprising:
a plurality of electrodes sensing cardiac signals; and
a microprocessor operably coupled to the plurality of electrodes and configured to determine a cumulative atrioventricular interval (AVI) burden in response to the sensed cardiac signals, and, in response to the determined cumulative AVI burden, to switch operation of the device between a minimal biventricular pacing (MBVP) mode, wherein the MBVP mode comprises scheduling delivery of biventricular pacing in a subsequent cardiac cycle in response to detecting absence of an intrinsic ventricular depolarization in a current cardiac cycle, and a conditional triple chamber pacing (CTCP) mode, wherein the CTCP mode comprises delivering biventricular pacing in the current cardiac cycle in response to detecting an absence of the intrinsic ventricular depolarization in the current cardiac cycle,
wherein the cumulative AVI burden comprises a measure of a proportion of atrioventricular intervals exceeding a predetermined threshold.

2. The device of claim 1, wherein the microprocessor determines first AVIs occurring during sinus rhythm and second AVIs occurring during delivery of atrial pacing therapy, and determines the cumulative AVI burden in response to the first and second AVIs.

3. The device of claim 2, wherein the microprocessor determines times of day associated with the first AVIs and times of day associated with the second AVIs and determines the cumulative AVI burden in response to the determined times of day.

4. The device of claim 1, wherein the microprocessor determines existence of a high burden AVI circumstance in response to both the cumulative AVI burden being greater than an AVI burden threshold and atrial pacing delivered being greater than an atrial pacing threshold, and operates the device in the CTCP mode in response to the high burden circumstance being determined.

5. The device of claim 4, wherein the AVI burden threshold corresponds to a percentage of AV intervals having a predetermined length during a predetermined time period and the atrial pacing threshold corresponds to a percentage of average daily atrial pacing being applied during the predetermined time period.

6. The device of claim 5, wherein the microprocessor further determines the existence of the high burden circumstance in response to determining whether atrial pacing occurring during a predetermined condition is greater than a predetermined condition threshold.

7. The device of claim 6, wherein the predetermined condition corresponds to sleep, and wherein, in response to atrial pacing being greater than the predetermined condition threshold during the predetermined condition, the microprocessor reduces an atrial pacing rate for a predetermined pacing time period, and determines the existence of the high burden circumstance in response to an extent of pacing being applied during the predetermined pacing time period at the reduced atrial pacing rate being greater than the atrial pacing threshold.

8. The device of claim 7, wherein the AVI burden threshold corresponds to approximately 10 percent of AV intervals over a one week period being greater than 230 ms and the atrial pacing threshold corresponds to atrial pacing being applied more than approximately 15 percent on an average daily basis during the predetermined pacing time period at the reduced atrial pacing rate.

9. The device of claim 5, wherein the AVI burden threshold corresponds to approximately 10 percent of AV intervals over a one week period of time being between 250 and 260 ms.

10. The device of claim 1, wherein the microprocessor determines existence of a high burden AVI circumstance in response to both the AVI burden over a predetermined time period being greater than an AVI burden threshold and an amount of biventricular pacing being delivered when the device is in the MBVP mode being greater then a biventricular pacing threshold, and operates the device in the CTCP mode in response to the high burden circumstance being determined.

11. The device of claim 10, wherein the AVI burden threshold corresponds to approximately 10 percent of AV intervals over a one week period being greater than 230 ms and the biventricular pacing threshold corresponds to approximately 10 to 15 percent biventricular pacing when in the MBVP mode.

12. The device of claim 4, wherein the microprocessor determines whether a percentage of atrial pacing is greater than a high burden AVI circumstance determination suspension threshold, and subsequently suspends determination of the high burden AVI circumstance in response to determining that the percentage of atrial pacing is greater than the high burden AVI circumstance determination suspension threshold.

13. The device of claim 12, wherein the high burden AVI circumstance determination suspension threshold corresponds to atrial pacing being applied approximately 80 percent of the time.

14. A method of operating a medical device, comprising:
sensing cardiac signals;
determining a cumulative atrioventricular interval (AVI) burden in response to the sensed cardiac signals; and
in response to the determined cumulative AVI burden, switching operation of the device between a minimal biventricular pacing (MBVP) mode, wherein the MBVP mode comprises scheduling delivery of biventricular pacing in a subsequent cardiac cycle in response to detecting absence of an intrinsic ventricular depolarization in a current cardiac cycle, and a conditional triple chamber pacing (CTCP) mode, wherein the CTCP mode comprises delivering biventricular pacing in the current cardiac cycle in response to detecting an absence of the intrinsic ventricular depolarization in the current cardiac cycle,
wherein the cumulative AVI burden comprises a measure of a proportion of atrioventricular intervals exceeding a predetermined threshold.

15. The method of claim 14, wherein determining the cumulative AVI burden comprises:
determining first AVIs occurring during sinus rhythm and second AVIs occurring during delivery of atrial pacing therapy; and
determining the cumulative AVI burden in response to the first and second AVIs.

16. The method of claim 15, further comprising:
determining times of day associated with the first AVIs;
determining times of day associated with the second AVIs; and
determining the cumulative AVI burden in response to the determined times of day.

17. The method of claim 14, further comprising:
determining existence of a high burden AVI circumstance in response to both the cumulative AVI burden being greater than an AVI burden threshold and atrial pacing delivered being greater than an atrial pacing threshold; and
operating the device in the CTCP mode in response to the high burden circumstance being determined.

18. The method of claim 17, wherein the AVI burden threshold corresponds to a percentage of AV intervals having a predetermined length during a predetermined time period and the atrial pacing threshold corresponds to a percentage of average daily atrial pacing being applied during the predetermined time period.

19. The method of claim 18, further comprising determining the existence of the high burden circumstance in response to determining whether atrial pacing occurring during a predetermined condition is greater than a predetermined condition threshold.

20. The method of claim 19, wherein the predetermined condition corresponds to sleep, and further comprising:
reducing an atrial pacing rate for a predetermined pacing time period in response to atrial pacing being greater than the predetermined condition threshold during the predetermined condition; and
determining the existence of the high burden circumstance in response to an extent of pacing being applied during the predetermined pacing time period at the reduced atrial pacing rate being greater than the atrial pacing threshold.

21. The method of claim 20, wherein the AVI burden threshold corresponds to approximately 10 percent of AV intervals over a one week period being greater than 230 ms and the atrial pacing threshold corresponds to atrial pacing being applied more than approximately 15 percent on an average daily basis during the predetermined pacing time period at the reduced atrial pacing rate.

22. The method of claim 18, wherein the AVI burden threshold corresponds to approximately 10 percent of AV intervals over a one week period of time being between 250 and 260 ms.

23. The method of claim 14, further comprising:
   determining existence of a high burden AVI circumstance in response to both the AVI burden over a predetermined time period being greater than an AVI burden threshold and an amount of biventricular pacing being delivered when the device is in the MBVP mode being greater then a biventricular pacing threshold; and operating the device in the CTCP mode in response to the high burden circumstance being determined.

24. The method of claim 23, wherein the AVI burden threshold corresponds to approximately 10 percent of AV intervals over a one week period being greater than 230 ms and the biventricular pacing threshold corresponds to approximately 10 to 15 percent biventricular pacing when in the MBVP mode.

25. The method of claim 17, further comprising determining whether a percentage of atrial pacing is greater than a high burden AVI circumstance determination suspension threshold, and subsequently suspends determining existence of the high burden AVI circumstance in response to determining that the percentage of atrial pacing is greater than the high burden AVI circumstance determination suspension threshold.

26. The method of claim 25, wherein the atrial pacing threshold corresponds to atrial pacing being applied approximately 80 percent of the time.

* * * * *

UNITED STATES PATENT AND TRADEMARK OFFICE
CERTIFICATE OF CORRECTION

| | | |
|---|---|---|
| PATENT NO. | : 8,396,553 B2 | |
| APPLICATION NO. | : 12/713517 | |
| DATED | : March 12, 2013 | |
| INVENTOR(S) | : Michael Sweeney | |

It is certified that error appears in the above-identified patent and that said Letters Patent is hereby corrected as shown below:

In the Claims

Claim 10, Col. 21, line 54, delete the word "then" and insert in place thereof -- than --;

Signed and Sealed this
Thirtieth Day of July, 2013

Teresa Stanek Rea
*Acting Director of the United States Patent and Trademark Office*